US008540640B2

(12) United States Patent
Sano et al.

(10) Patent No.: US 8,540,640 B2
(45) Date of Patent: Sep. 24, 2013

(54) ULTRASONIC PROBE AND METHOD FOR MANUFACTURING THE SAME AND ULTRASONIC DIAGNOSTIC DEVICE

(75) Inventors: Shuzo Sano, Tokyo (JP); Akifumi Sako, Tokyo (JP); Takashi Kobayashi, Tokyo (JP); Mikio Izumi, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 647 days.

(21) Appl. No.: 12/525,353

(22) PCT Filed: Feb. 27, 2008

(86) PCT No.: PCT/JP2008/053366
§ 371 (c)(1),
(2), (4) Date: Mar. 4, 2010

(87) PCT Pub. No.: WO2008/114582
PCT Pub. Date: Sep. 25, 2008

(65) Prior Publication Data
US 2010/0179430 A1 Jul. 15, 2010

(30) Foreign Application Priority Data
Mar. 20, 2007 (JP) ................................ 2007-072604

(51) Int. Cl.
*A61B 8/14* (2006.01)
(52) U.S. Cl.
USPC ........................... 600/459; 600/407; 600/437
(58) Field of Classification Search
USPC ......................... 600/459, 437, 407
See application file for complete search history.

(56) References Cited

U.S. PATENT DOCUMENTS 5,287,000 A * 2/1994 Takahashi et al. ............ 257/676
5,894,452 A    4/1999 Ladabaum et al.
(Continued)

FOREIGN PATENT DOCUMENTS

JP    2004-350700    12/2004
JP    2005-295553    10/2005
(Continued)

OTHER PUBLICATIONS

International Search Report issues in International Application No. PCT/JP2008/053366 on Mar. 21, 2008.

(Continued)

*Primary Examiner* — Tse Chen
*Assistant Examiner* — Joel F Brutus
(74) *Attorney, Agent, or Firm* — Antonelli, Terry, Stout & Kraus, LLP.

(57) ABSTRACT

An ultrasonic probe (2) comprises a cMUT chip (20), which has a plurality of vibration elements whose electromechanical coupling coefficient or the sensitivity changes depending on a bias voltage, and transmits/receives an ultrasonic wave; an acoustic lens (26) provided on the ultrasonic wave radiation side of the cMUT chip (20); a backing layer (22) provided on the back side of the cMUT chip (20) for absorbing propagation of the ultrasonic wave; an electric wiring portion (flexible substrate (72)), which is provided from the peripheral portion of the cMUT chip (20) to the side face of the backing layer (22) and has a signal pattern connected with the electrode of the cMUT chip (20) arranged thereon; and a housing (ultrasonic probe cover (25)) for containing the cMUT chip (20), the acoustic lens (26), the backing layer (22) and the electric wiring portion (flexible substrate (72)). A ground layer (conductive film (76)) of ground potential is provided on the ultrasonic wave radiation side of the cMUT chip (20).

21 Claims, 19 Drawing Sheets

(56) References Cited

U.S. PATENT DOCUMENTS

| | | | |
|---|---|---|---|
| 2003/0048698 A1* | 3/2003 | Barnes et al. | 367/181 |
| 2004/0261251 A1 | 12/2004 | Schindel | |
| 2005/0046311 A1* | 3/2005 | Baumgartner et al. | 310/334 |
| 2006/0004290 A1* | 1/2006 | Smith et al. | 600/459 |
| 2006/0118939 A1* | 6/2006 | Fisher et al. | 257/690 |
| 2007/0182287 A1* | 8/2007 | Lukacs et al. | 310/334 |

FOREIGN PATENT DOCUMENTS

| | | |
|---|---|---|
| JP | 2006-75425 | 3/2006 |
| JP | 2006-166985 | 6/2006 |
| JP | 2006-198240 | 8/2006 |
| JP | 2006-212077 | 8/2006 |
| JP | 2006-319712 | 11/2006 |
| JP | 2006-343315 | 12/2006 |
| WO | WO 2005/077012 | 8/2005 |
| WO | WO 2005/120355 | 12/2005 |

OTHER PUBLICATIONS

Office Action issued in Chinese Patent Application No. 200880008931.9 on Feb. 1, 2011.

Japanese Office Action, dated Dec. 13, 2011, issued in corresponding Japanese Patent Application No. 2009-505109.

English-translated International Preliminary Report on Patentability in connection with PCT/JP2008/053366.

Written Opinion of the International Searching Authority in connection with PCT/JP2008/053366.

* cited by examiner

ULTRASONIC PROBE AND METHOD FOR MANUFACTURING THE SAME AND ULTRASONIC DIAGNOSTIC DEVICE

TECHNICAL FIELD

The present invention relates to an ultrasonic probe which takes a diagnostic image and a method for manufacturing the same and an ultrasonic diagnostic device.

BACKGROUND ART

An ultrasonic diagnostic device is a device which takes a diagnostic image based on a reflection echo signal output from an ultrasonic probe. A plurality of ultrasonic transducers are arranged at the ultrasonic probe. The ultrasonic transducer converts a driving signal into an ultrasonic wave, transmits ultrasonic wave to a subject, receives the reflection echo signal generated from the subject and converts it to an electric signal.

Recently, an ultrasonic probe that uses a cMUT (Capacitive Micromachined Ultrasonic Transducer) has been developed. The cMUT is a super-minute capacity type ultrasonic wave transducer manufactured using a semiconductor microfabrication process. In the cMUT, an ultrasonic wave transmitting/receiving sensitivity, in other words, electromechanical coupling coefficient changes depending on the magnitude of a bias voltage. In addition, the bias voltage is superimposed on the driving signal provided by an ultrasonic wave transmitting/receiving part and is applied (For example, refer to patent document 1).
Patent Document 1: U.S. Pat. No. 5,894,452

DISCLOSURE OF THE INVENTION

Problems to be Solved by the Invention

However, in the cMUT probe described in the above-mentioned patent document 1, a DC voltage is applied to a lower electrode as the bias voltage for the silicon substrate, and an AC high frequency voltage is applied to an upper electrode as the driving signal against the lower electrode. As a result, the upper electrode is not a ground layer at ground potential, and there is a problem that an electric safety for a subject is insufficient.

The present invention has been accomplished in view of the above-described problems, and the object of the present invention is to provide an ultrasonic probe which is possible to improve the electric safety for the subject, and a method for manufacturing the same and an ultrasonic diagnostic device.

Means for Solving the Problems

The ultrasonic probe according to the present invention is an ultrasonic probe comprising a cMUT chip having a plurality of vibration elements whose electromechanical coupling coefficient or a sensitivity changes depending on a bias voltage, and transmitting/receiving an ultrasonic wave, an acoustic lens provided on an ultrasonic wave radiation side of said cMUT chip, a backing layer provided on a back side of said cMUT chip and absorbing a propagation of said ultrasonic wave, an electric wiring portion provided from a peripheral portion of said cMUT chip and on a side surface of said backing layer and having a signal pattern connected with an electrode of said cMUT chip arranged thereon and a housing for containing said cMUT chip, said acoustic lens, said backing layer and said electric wiring portion, wherein a ground layer at ground potential is provided on an ultrasonic wave radiation side of said cMUT chip.

The method for manufacturing the ultrasonic probe according to the present invention is A method for manufacturing a cMUT chip having a plurality of vibration elements whose electromechanical coupling coefficient or a sensitivity changes depending on a bias voltage, and transmitting/receiving an ultrasonic wave, an acoustic lens provided on an ultrasonic wave radiation side of said cMUT chip, a backing layer provided on a back side of said cMUT chip and absorbing a propagation of said ultrasonic wave, an electric wiring portion provided from a peripheral portion of said cMUT chip and on a side surface of said backing layer and having a signal pattern connected with an electrode of said cMUT chip arranged thereon, and a housing for containing said cMUT chip, said acoustic lens, said backing layer and said electric wiring portion, said method being characterized by comprising a step of bonding said cMUT chip on an upper surface of said backing layer, a step of bonding said electric wiring portion on an upper periphery of said backing layer, a step of connecting said electric wiring portion and said cMUT chip through a wire, a step of filling around said wire with light curing resin as a sealant, a step of forming a conductive film which can connect the ground on an inner surface of said acoustic lens, and a step of bonding said acoustic lens on an ultrasonic wave radiation surface of said cMUT chip.

The ultrasonic diagnostic device according to the present invention comprises an ultrasonic probe comprising a cMUT chip having a plurality of vibration elements whose electromechanical coupling coefficient or a sensitivity changes depending on a bias voltage, and transmitting/receiving an ultrasonic wave, an acoustic lens provided on an ultrasonic wave radiation side of said cMUT chip, a backing layer provided on a back side of said cMUT chip and absorbing a propagation of said ultrasonic wave, an electric wiring portion provided from a peripheral portion of said cMUT chip and on a side surface of said backing layer and having a signal pattern connected with an electrode of said cMUT chip arranged thereon and a housing for containing said cMUT chip, said acoustic lens, said backing layer and said electric wiring portion, wherein a ground layer at ground potential is provided on an ultrasonic wave radiation side of said cMUT chip.

Effects of the Invention

According to the present invention, it is possible to provide an ultrasonic probe and a method for manufacturing the same and an ultrasonic diagnostic device.

DESCRIPTION OF REFERENCE NUMERALS

Figure 1:
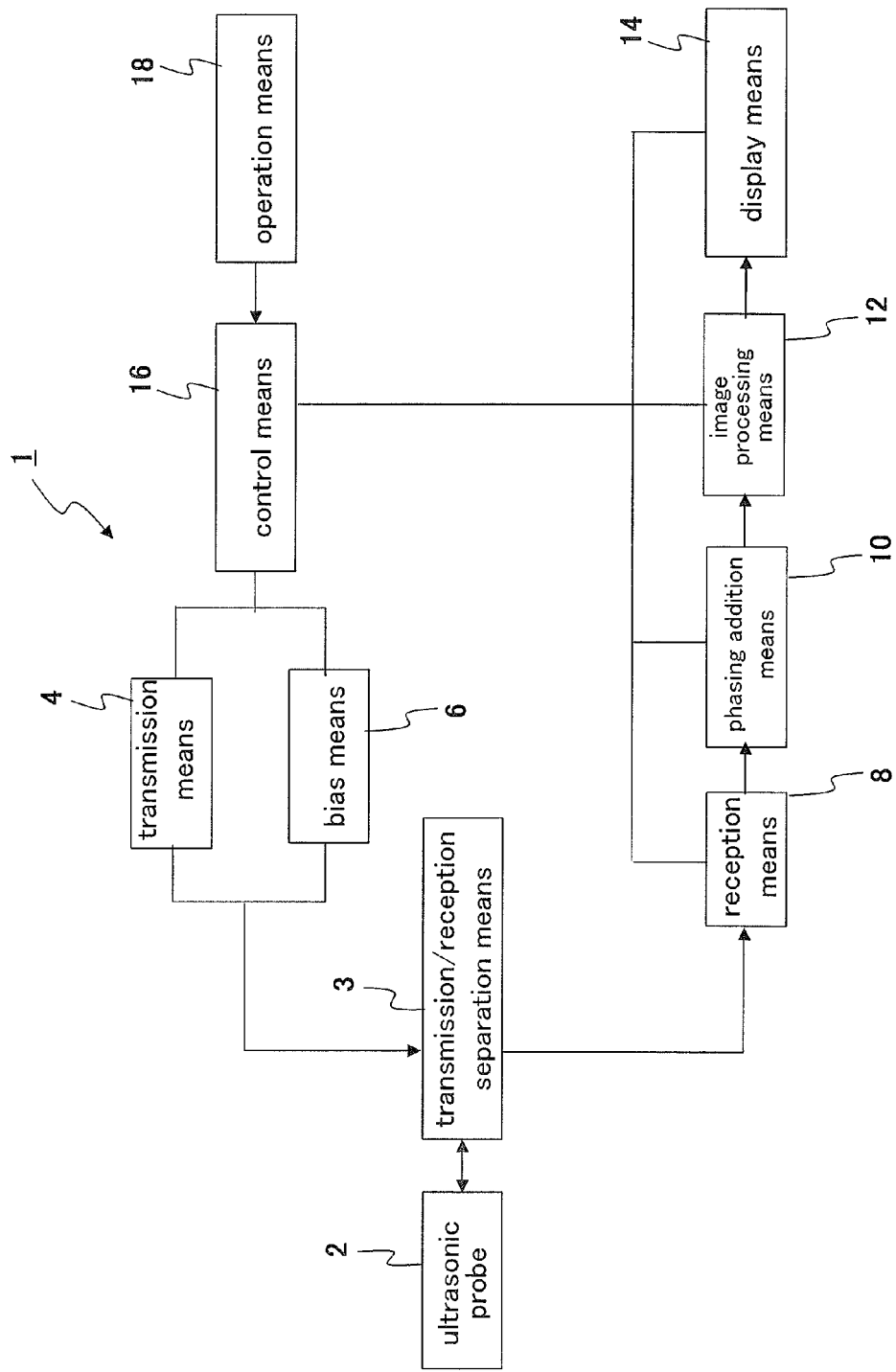
FIG. 1 is a block diagram of an ultrasonic diagnostic device 1.

1: ultrasonic diagnostic device
2: ultrasonic probe
3: transmission-reception separation means
4: transmission means
6: bias means
8: reception means
10: phasing addition means
12: image processing means
14: display means
16: control means
18: operation means
20: cMUT chip
21-1, 21-2 . . . : transducer
22: backing layer
25: ultrasonic probe cover
26: acoustic lens
27: sealant
28: vibration element
38, 41: signal pattern
40: substrate
46: upper electrode
48: lower electrode
72: flexible substrate
70, 71, 90: bonding layer
76: conductive film (ground layer)
78: insulator film (insulator layer)
84, 94: ground line (cable shielded line)
86: wire
88: light curing resin
108, 120: ground
161, 171, 181, 185, 191, 195: through hole
163, 165, 173, 175, 182, 184, 192, 194: pad terminal
164, 174, 193: conductive adhesive (anisotropic conductive adhesive sheet)
183: wire

BEST MODE FOR CARRYING OUT THE INVENTION

Hereinafter, preferred embodiments of an ultrasonic probe and an ultrasonic diagnostic device according to the present invention will be described in detail with reference to the attached drawings. In the following description and the attached drawings, structural elements having generally identical functional configurations are denoted by same reference numerals, and their repeated descriptions are omitted.

1. Configuration of an Ultrasonic Diagnostic Device 1

First, the configuration of an ultrasonic diagnostic device 1 will be described with reference to FIG. 1. FIG. 1 is a block diagram of the ultrasonic diagnostic device 1. The ultrasonic diagnostic device 1 is composed of an ultrasonic prove 2, transmission/reception separation means 3, transmission means 4, bias means 6, reception means 8, phasing addition means 10, image processing means 12, display means 14, control means 16, and operation means 18.

The ultrasonic probe 2 is a device which touches a subject and transmits/receives an ultrasonic wave with a subject. An ultrasonic wave is projected to the subject from the ultrasonic probe 2, and a reflection echo signal generated from the subject is received by the ultrasonic probe 2. The transmission means 4 and the bias means 6 are devices that supply a driving signal to the ultrasonic probe 2. The reception means 8 is a device that receives the reflection echo signal output by the ultrasonic probe 2. In addition, the reception means 8 processes an analog-digital conversion etc. to the received reflection echo signal. The transmission/reception separation means 3 switches and separates a transmission and a reception so as to give a driving signal to the ultrasonic probe 2 from the transmission means 4 at the time of transmission, and give a reception signal to the reception means 8 from the ultrasonic probe 2 at the time of reception.

The phasing addition part 10 is a device that phases and adds the received reflection echo signal. The image processing means 12 is a device that produces a diagnosis image (for instance, a cross-sectional image and a blood flow image) on the basis of the reflection echo signal which is phased and added. The display part 14 is a display device that displays the diagnosis image which is image-processed. The control means 16 is a device that controls each structural elements mentioned above. The operation means 18 is a device that gives a direction to the control means 16. The operation means 18 is an input device for instance, a track ball, a keyboard, or a mouse etc.

2. Ultrasonic Probe 2

Next, the ultrasonic probe 2 will be described with reference to FIG. 2 to FIG. 4.

(2-1. Configuration of the Ultrasonic Probe 2)

Figure 2:
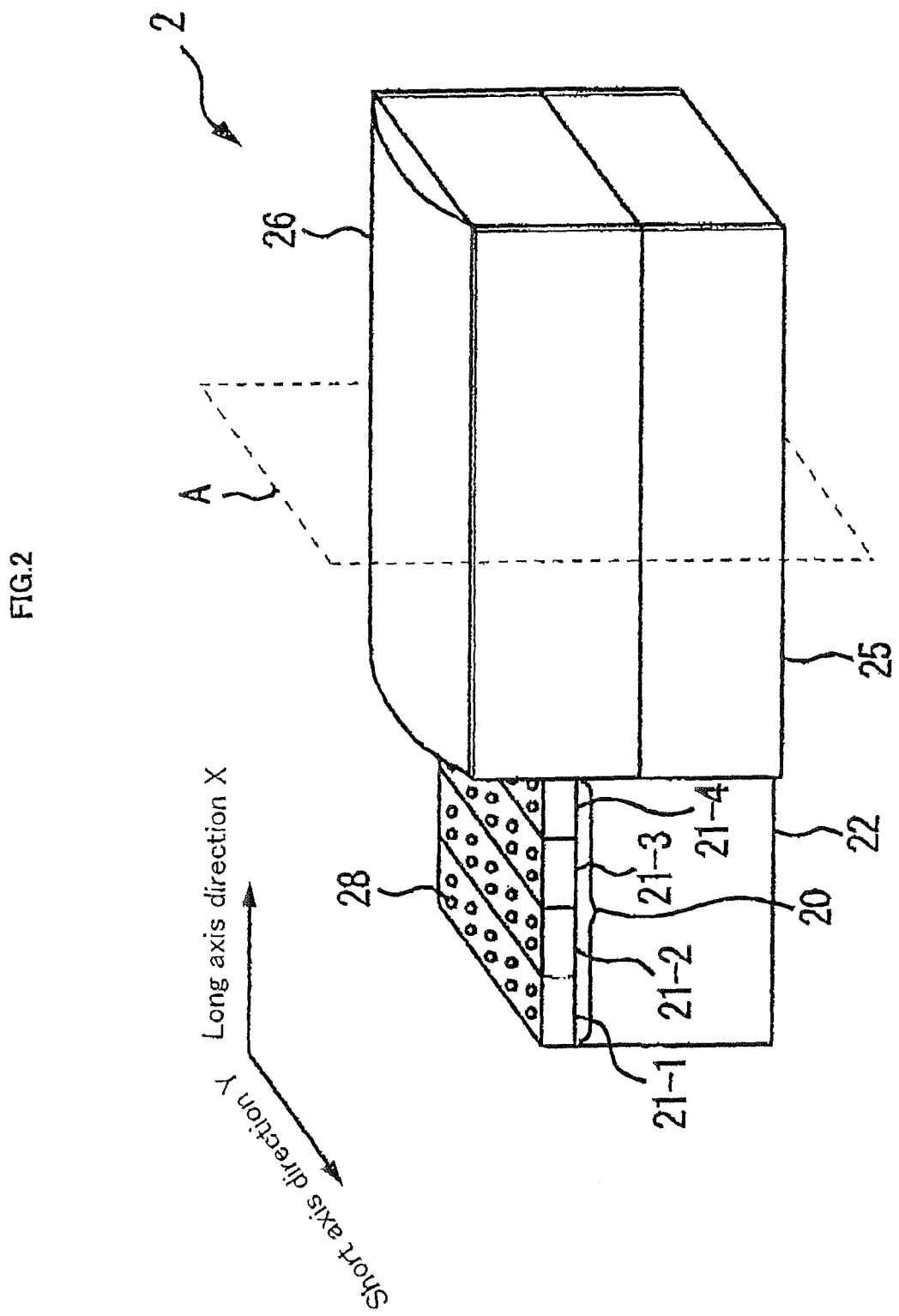
FIG. 2 is a block diagram of an ultrasonic probe 2.

FIG. 2 is a block diagram of the ultrasonic probe 2. FIG. 2 is a partial cut-away perspective view of the ultrasonic probe 2. The ultrasonic probe 2 has a cMUT chip 20. The cMUT chip 20 is one dimensional array type transducer group where a plurality of transducers 21-1 and 21-2 etc. are arranged like a reed shape. A plurality of vibration elements 28 are set in the transducers 21-1 and 21-2 etc. In addition, the transducer group in other types such as a two dimensional array type or a convex type etc. may be used. A backing layer 22 is provided on the back side of the cMUT chip 20. An acoustic lens 26 is provided on the ultrasonic wave radiation side of the cMUT chip 20. The cMUT chip 20 and the backing layer 22 etc. are stored in an ultrasonic probe cover 25.

The cMUT chip 20 converts the driving signal from the transmission means 4 and the bias means 6 into an ultrasonic wave and transmits the ultrasonic wave to the subject. The reception means 8 converts the ultrasonic wave generated from the subject into an electric signal and receives it as the reflection echo signal. The backing layer 22 is a layer which absorbs the propagation of the ultrasonic wave projected from the cMUT chip 20 to the back side so as to control an extra vibration. The acoustic lens 26 is a lens which converges the ultrasonic beam transmitted from the cMUT chip 20. As for the acoustic lens 26, a curvature is provided based on one focal length.

In addition, a matching layer may be provided between the acoustic lens 26 and the cMUT chip 20. The matching layer is a layer which adjusts the acoustic impedances of the cMUT chip 20 and the subject so as to improve a transmitting efficiency of the ultrasonic wave.

(2-2. Transducer 21)

Figure 3:
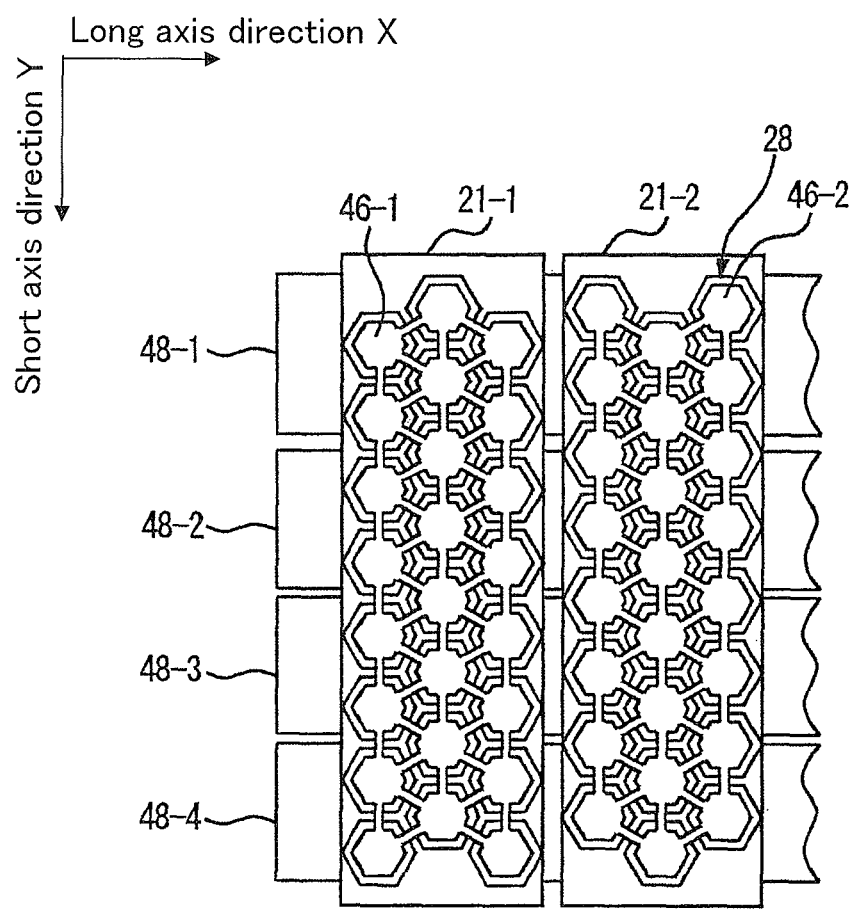
FIG. 3 is a block diagram of a transducer 21.

FIG. 3 is a block diagram of the transducer 21. An upper electrode 46 of the vibration element 28 is connected with each transducer 21 divided into with respect to the direction X of the long axis. That is, the upper electrode 46-1 and the upper electrode 46-2 etc. are arranged in parallel in direction X of the long axis. A lower electrode 48 of the vibration element 28 is connected in each division divided into with respect to the direction Y of the short axis. That is, the lower electrode 48-1 and the lower electrode 48-2, etc. are arranged in parallel in direction Y of the short axis.

(2-3. Vibration Element 28)

Figure 4:
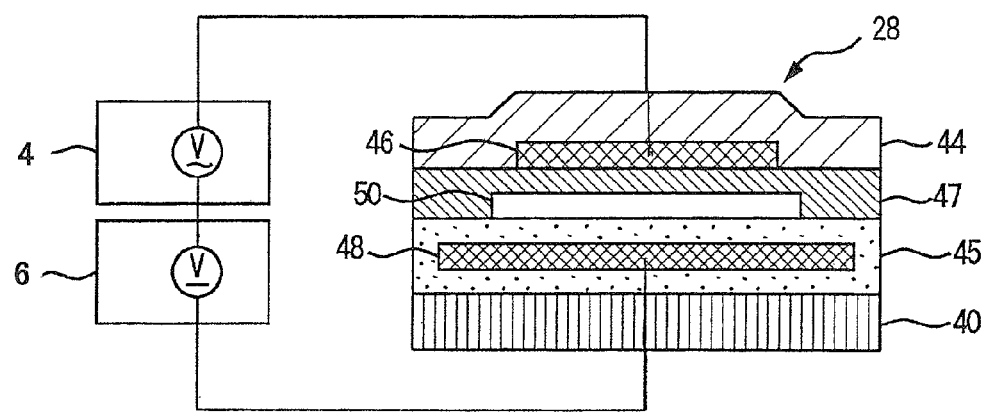
FIG. 4 is a block diagram of a vibration element 28.

FIG. 4 is a block diagram of the vibration element 28. FIG. 4 is a cross sectional view of one vibration element 28. The vibration element 28 is composed of a substrate 40, a film body 44, a film body 45, the upper electrode 46, a frame body 47, and the lower electrode 48. The vibration element 28 is formed using a microfabrication by a semiconductor process. In addition, the vibration element 28 corresponds to one elemental device of the cMUT.

The substrate 40 is a semiconductor substrate such as silicon. The film body 44 and the frame body 47 are made of semiconductor compound such as silicon compound. The film body 44 is provided on the ultrasonic wave radiation side of the frame body 47. The upper electrode 46 is provided between the film body 44 and the frame body 47. The lower electrode 48 is provided in the film body 45 formed on the substrate 40. An internal space 50 comparted by the flame body 47 and the film body 45 is vacuum state or is filled with a predetermined gas. Each of the upper electrode 46 and the lower electrode 48 is connected with the transmission means 4 which supplies an AC high frequency voltage as a driving signal and the bias means 6 which applies a DC voltage as a bias voltage.

When an ultrasonic wave is transmitted, a DC bias voltage (Va) is applied to the vibration element 28 through the upper electrode 46 and the lower electrode 48, and an electric field is generated by a bias voltage (Va). The film body 44 is tensioned by the generated electric field and has predetermined electromechanical coupling coefficient (Sa). When the driving signal is supplied from the transmission means 4 to the upper electrode 46, the ultrasonic wave is projected from the film body 44 based on the electromechanical coupling coefficient (Sa). Moreover, when the bias voltage (Vb) of DC is applied to the vibration element 28 through the upper electrode 46 and the lower electrode 48, the electric field is generated by the bias voltage (Vb). The film body 44 is tensioned by the generated electric field and has predetermined electromechanical coupling coefficient (Sb). When the driving signal is supplied from the transmission means 4 to the upper electrode 46, the ultrasonic wave is projected from the film body 44 based on the electromechanical coupling coefficient (Sb).

Here, when the bias voltage is "Va<Vb", the electromechanical coupling coefficient becomes "Sa<Sb". On the other hand, when the ultrasonic wave is received, the film body 44 is excited by the reflection echo signal generated from the subject and a capacity of the internal space 50 changes An electric signal is detected through the upper electrode 46 based on the amount of the change of this internal space 50.

In addition, the electromechanical coupling coefficient of the vibration element 28 is determined by the tension degree of the film body 44. Therefore, if the magnitude of the bias voltage applied to the vibration element 28 is changed and the tension degree of the film body 44 is controlled, the sound pressure (for instance, amplitude) of the ultrasonic wave projected from the vibration element 28 can be changed even if the driving signals with same amplitude are input.

3. First Embodiment

Next, the first embodiment will be described with reference to FIG. 5 and FIG. 6.

(3-1. Component of the Ultrasonic Probe 2)

Figure 5:
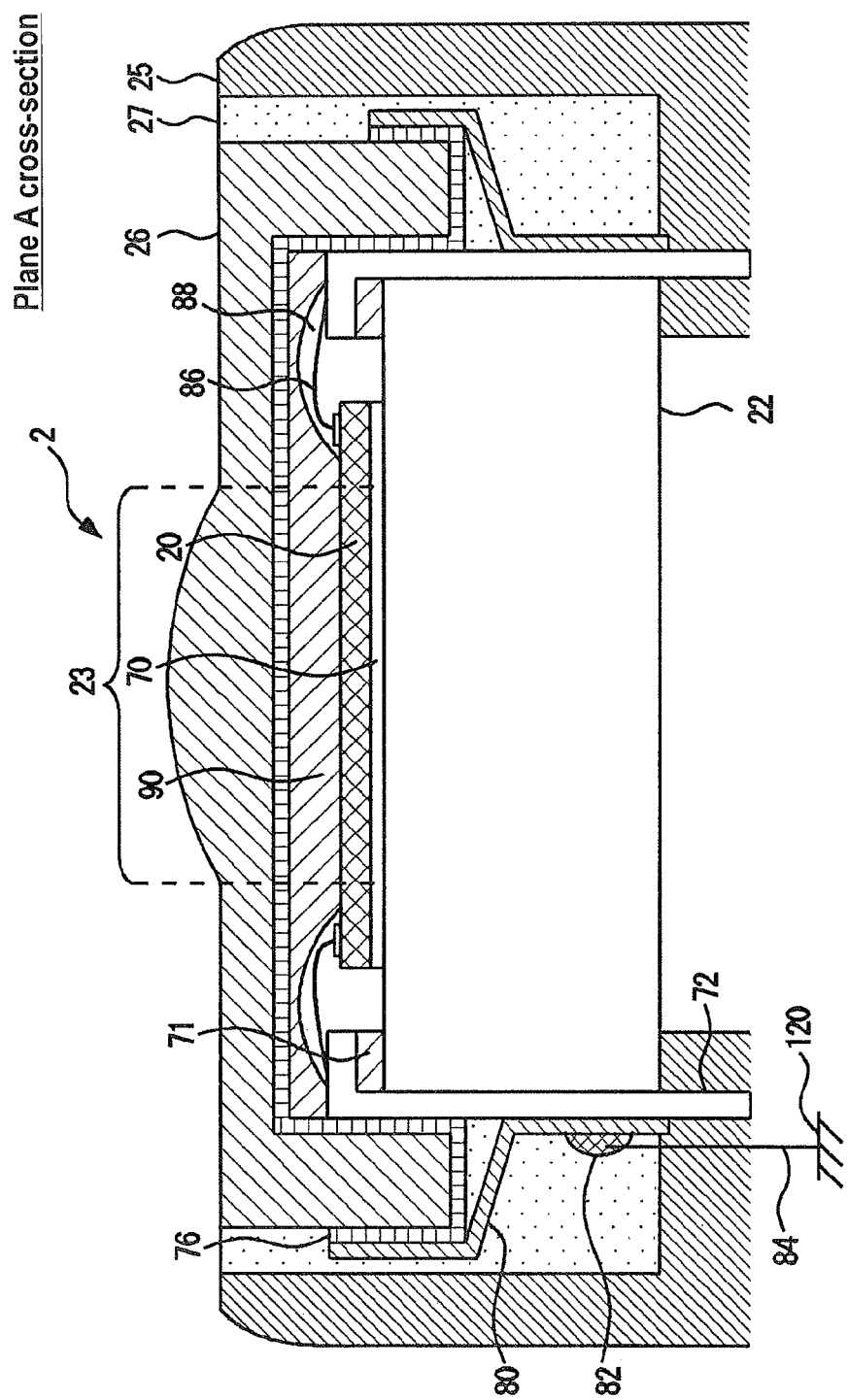
FIG. 5 is a view showing the ultrasonic probe 2 according to the first embodiment.

The ultrasonic probe 2 according to the first embodiment is shown in FIG. 5. FIG. 5 is the cross sectional view of plane A of the ultrasonic probe 2 of FIG. 2.

A conductive film 76 is formed along inner surface and outer side surface of the acoustic lens 26. The conductive film 76 is a Cu film formed by a deposition for instance. The conductive film 76 is connected with a ground 120 of the main body device side through a conductive member 80 and a ground line 84.

The conductive member 80 is a member having conductivity. The conductive member 80 is a reliable member which is hard to break compared to the conductive layer 76. For instance, the conductive member 80 is a Cu tape more rigid than the conductive film 76. The conductive member 80 is fixed to the conductive film 76 on the outer side surface of the acoustic lens 26 and the outer side surface of a flexible substrate 72. The ground line 84 is connected with the conductive member 80 through a connecting portion 82 by such as soldering and a conductive adhesive.

The cMUT chip 20 is bonded on the upper surface of the backing layer 22 through a bonding layer 70. The flexible substrate 72 (Flexible printed circuits: FPC) is provided along an upper periphery and four side surfaces of the backing layer 22. The flexible substrate 72 is bonded on the upper periphery of the backing layer 22 through a bonding layer 71.

The bonding layer 70 and the bonding layer 71 are adhesives made of epoxy resin for instance. The height direction position of the cMUT chip 20 and the flexible substrate 72 can be adjusted by arbitrarily adjusting the layer thickness of the bonding layer 70 and the bonding layer 71.

The flexible substrate 72 and the cMUT chip 20 are electrically connected through a wire 86. The wire 86 is connected by a wire bonding method. The Au wire etc. can be used as wire 86. Light curing resin 88 is filled around the wire 86 as a sealant. In addition, a flip chip bonding method connecting each pad may be used as substitute for the wire bonding method.

The acoustic lens 26 is bonded on the ultrasonic wave radiation surface of the cMUT chip 20 through bonding layer 90. For instance, silicon rubber is used as the material of the acoustic lens 26. As for the material of the bonding layer 90, it is preferable to be similar to the material of the acoustic lens 26 (for instance, silicon). The ultrasonic wave radiation surface of the acoustic lens 26 is convex to the ultrasonic wave irradiation direction at least within the range of area 23. The vibration element 28 is arranged in the cMUT chip 20 within the range at least corresponding to the area 23. An ultrasonic wave is projected from the convex portion of the acoustic lens 26. The back surface of the acoustic lens 26 has the concave portion at the position corresponding to the periphery of the cMUT chip 20. A connecting portion (portion of light curing resin 88) between the cMUT chip 20 and the flexible substrate 72 engages with this concave portion.

The ultrasonic probe cover 25 is provided on the four sides of the ultrasonic probe 2. The ultrasonic probe cover 25 is fixed on the four side surfaces of the acoustic lens 26. An examiner operates the ultrasonic probe 2 gripping the ultrasonic probe cover 25 by hand. A sealant 27 is filled in the space between the ultrasonic probe cover 25 and the acoustic lens 26. In addition, it is preferable to locate the top position of the ultrasonic probe cover 25 above the cMUT chip 20. As a result, even if an accident such as a fall of the ultrasonic probe 2 occurs, the direct impact can be prevented and the cMUT chip 20 can be protected.

(3-2. Connection of the Ultrasonic Probe 2)

Figure 6:
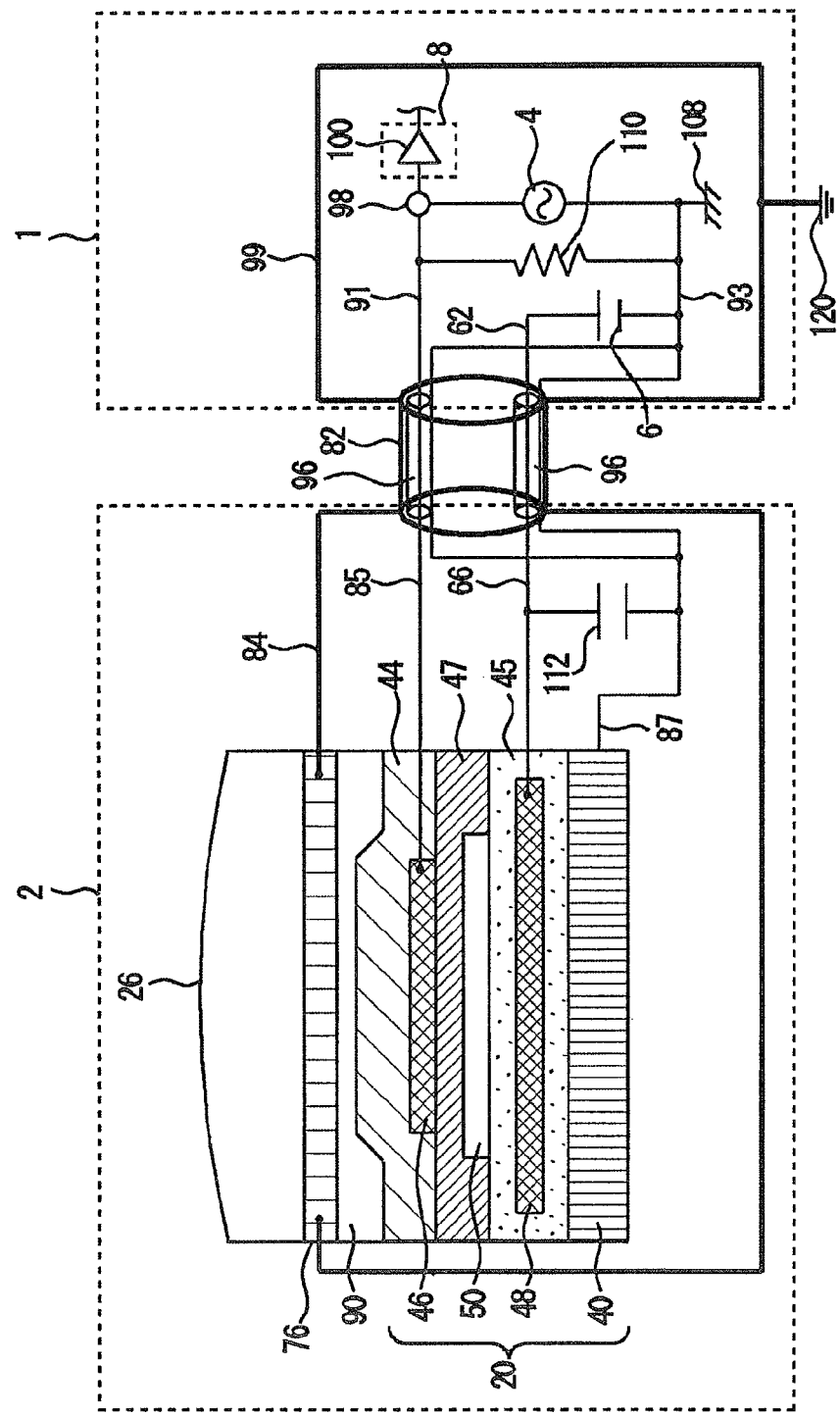
FIG. 6 is a schematic view showing the connection between the ultrasonic diagnostic device 1 and the ultrasonic probe 2.

FIG. 6 is the schematic view showing the connection between the ultrasonic diagnostic device 1 and the ultrasonic probe 2. The ultrasonic diagnostic device 1 and the ultrasonic probe 2 are connected through a cable 82. The cable 82 has a plurality of coaxial cables 96.

The upper electrode 46 of the vibration element 28 is connected with a wiring 85. The wiring 85 is connected with a wiring 91 in the ultrasonic diagnostic device 1 through internal conductor of the coaxial cable 96. The wiring 91 is connected with a reception amplifier 100 in the reception means 8 and the transmission means 4 through a transmission/reception separation circuit 98. The lower electrode 48 of the vibration element 28 is connected with a wiring 66. The wiring 66 is connected with a wiring 62 in the ultrasonic diagnostic device 1 through internal conductor of the coaxial cable 96. The wiring 62 is connected with the bias means 6. The number of coaxial cables 96 equals to the total number of the upper electrodes 46 and the lower electrodes 48 mutually arranged in a plurality of vibration elements 28. The substrate 40 of the vibration element 28 is connected with a wiring 87. The wiring 87 is connected with a wiring 93 in the ultrasonic diagnostic device 1 through outer conductor of the coaxial cable 96. The wiring 93 is connected with ground 108 through the chassis ground of the main body device (not shown here).

A capacitor 112 is arranged between the wiring 66 and the wiring 87. This capacitor 112 is a capacitative element for a bypass of a signal current to bypass the current from the lower electrode 48 when an AC current flowed from the upper electrode 46 to the lower electrode 48. A resistance 110 is arranged between the wiring 91 and the wiring 93. This resistance 110 is a resistive element to stabilize the DC potential of the upper electrode 46 at a ground potential. The bias means 6 is arranged between the wiring 62 and the wiring 93. This bias means 6 causes the potential difference between the upper electrode 46 and the lower electrode 48. Furthermore, the transmission means 4 applies an AC high frequency voltage to the upper electrode 46 as a driving signal. Specifically, in the upper electrode 46, DC=ground (standard potential) and AC=Vpp, and in the lower electrode 48, DC=Vdc and AC=0.

The conductive film 76 of the vibration element 28 is connected with a wiring 84. The wiring 84 is formed so as to cover the internal circuit (the wiring 85, the wiring 66, the capacitor 112, etc.) of the ultrasonic probe 2 and is connected with a wiring 99 in the ultrasonic diagnostic device 1 through a circumference of the cable 82. The wiring 99 is formed so as to cover the internal circuit (the wiring 91, the wiring 62, and the resistance 110, etc.) of the ultrasonic diagnostic device 1, and connected with a ground 120. Therefore, in the conductive film 76, the wiring 84, the circumference of the cable 82 and the wiring 99, DC=0 and AC=0. The conductive film 76, the wiring 84, the circumference of the cable 82, the wirings 99 and the ground 120 form a protection circuit and do not allow an electromagnetic wave from the outside to invade the internal circuit of the ultrasonic diagnostic device 1 and the ultrasonic probe 2, and do not allow the electricity generated in the ultrasonic diagnostic device 1 and the ultrasonic probe 2 to discharge to the outside of them.

(3-3. Effects of the First Embodiment)

As described above, in the ultrasonic probe 2 of the first embodiment, the conductive film 76 is provided on the ultrasonic wave radiation side of the cMUT chip 20 as a ground layer. Therefore, even if the acoustic lens 26 is damaged, because the conductive film 76 is at ground potential, an electric shock is prevented and the electric safety of the ultrasonic probe to the subject can improve. Moreover, the close space of the ground potential is formed with the conductive film 76, the ground line 84 and the chassis ground of the main body device. That is, because the major structural elements and the main body circuit of the ultrasonic probe 2 are involved in the close space of the ground potential, an unnecessary electric wave from the outside can be prevented from influencing them, and the electromagnetic wave generated by the ultrasonic probe 2 itself can be prevented from influencing an external device harmfully.

Moreover, in the ultrasonic probe 2 of the first embodiment, the conductive film 76 is formed along the inner surface and the outer side surface of the acoustic lens 26 and connected with the ground 120 through the high reliable conductive member 80 and the ground line 84. As a result, the conductive film 76 formed along the inner surface and outer side surface of the acoustic lens 26, not a sheet type conductive film drawn by in mold forming, is easily and firmly connected with the ground line 84 through the conductive member 80. The certainty and the working efficiency of mounting can improve. Moreover, by using the high reliable conductive member 80, the damage of the conductive member 80 when it is firmed on the flexible substrate 72 can be prevented. Moreover, in FIG. 5, though the conductive member 80 and the ground line 84 were shown only on a left side surface of flexible substrate 72 on paper, they can be provided at either at least one of the four side surfaces of the flexible substrate 72

4. Second Embodiment

Figure 7:
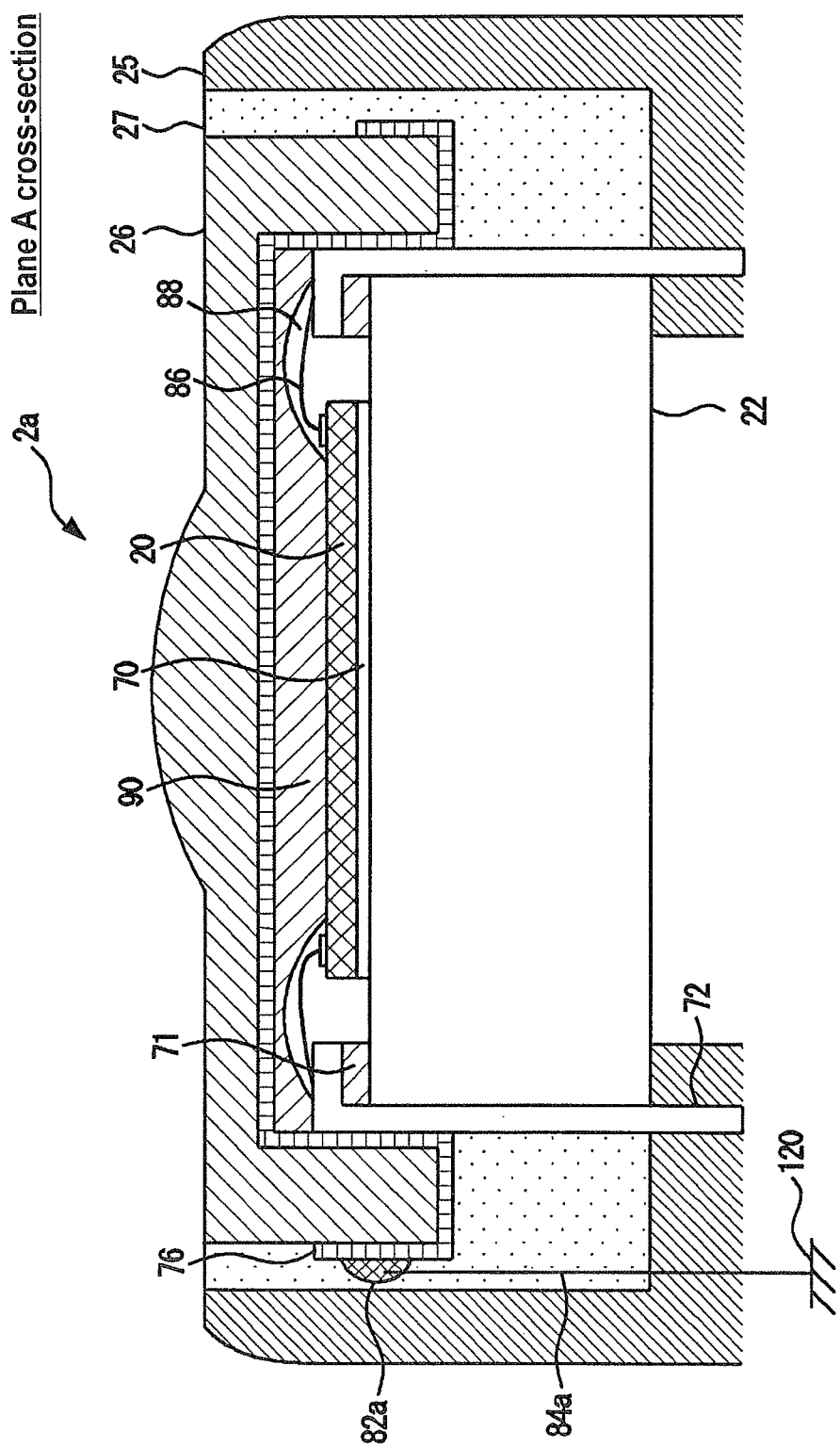
FIG. 7 is a view showing an ultrasonic probe 2a according to the second embodiment.

Next, the second embodiment will be described with reference to FIG. 7. FIG. 7 is a view showing the ultrasonic probe 2a according to the second embodiment. FIG. 7 corresponds to plane A cross section of FIG. 2.

In the first embodiment, it is described that the conductive film 76 connects with the ground line 84 through the conductive member 80, however, the conductive film 76 and the ground line 84a is directly connected in the second embodiment. The ground line 84a is directly connected with the conductive film 76 in the outer side surface of the acoustic lens 26 through a connecting portion 82a by soldering or a conductive adhesive etc.

As described above, in the second embodiment as well as the first embodiment, because the conductive film 76 is provided on the ultrasonic wave radiation side of the cMUT chip 20 as a ground layer, the electric safety of the ultrasonic probe 2a to the subject can improve. Moreover, in the second embodiment, a conductive member to connect the conductive film 76 and the ground line 84a do not need to be provided.

5. Third Embodiment

Figure 8:
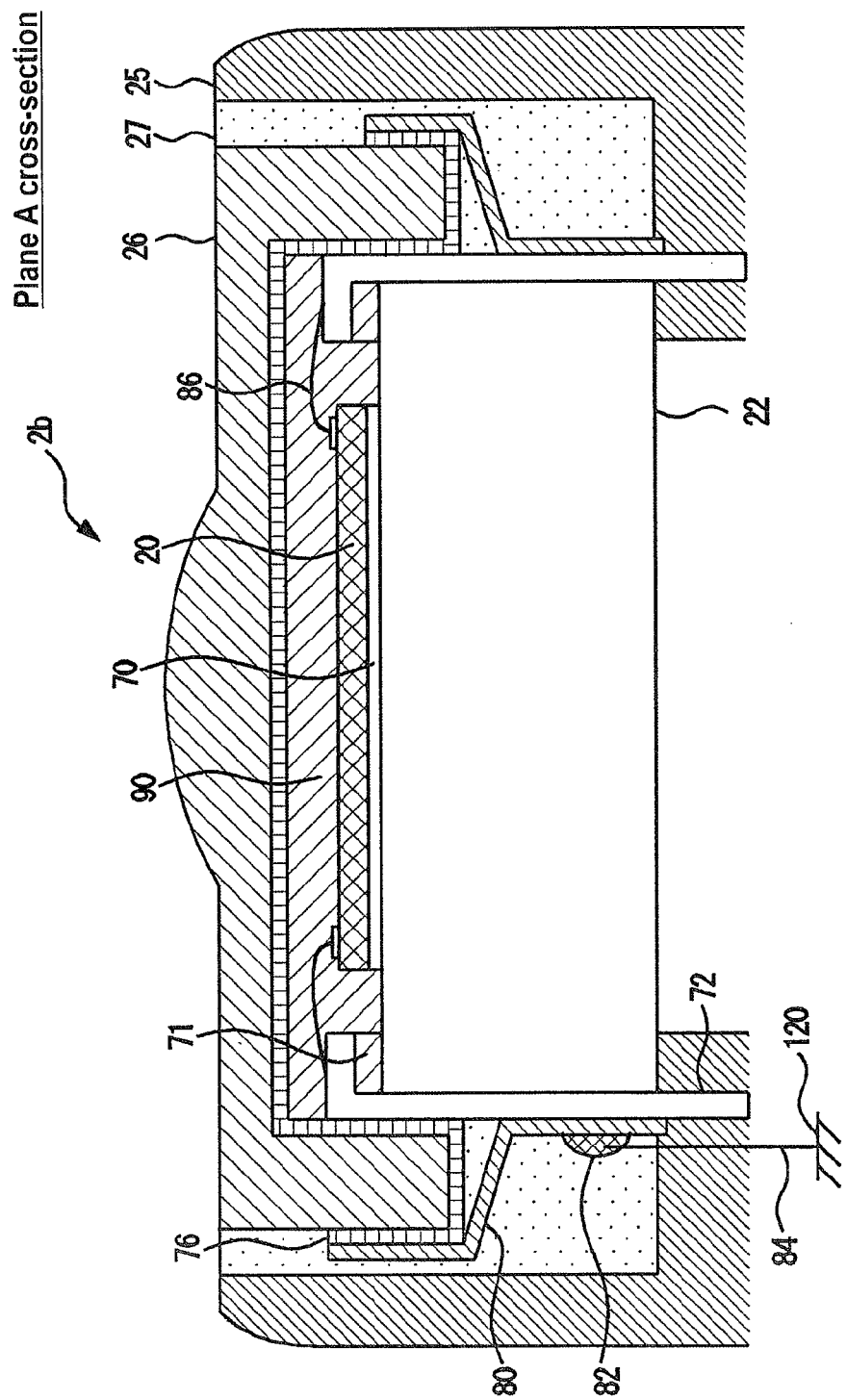
FIG. 8 is a view showing an ultrasonic probe 2b according to the third embodiment.

Next, the third embodiment will be described with reference to FIG. 8. FIG. 8 is a view showing the ultrasonic probe 2b according to the third embodiment. FIG. 8 corresponds to plane A cross section of FIG. 2.

In the first embodiment, it is described that the light curing resin 88 is filled around the wire 86 as a sealant, however, the sealant is not filled around the wire 86 in the third embodiment. A bonding layer 90 is filled in not only between the acoustic lens 26 and the cMUT chip 20 but also around the wire 86. The bonding layer 90 not only bonds the acoustic lens 26 and the cMUT chip 20 but also functions as a sealant around the wire 86.

As described above, in the third embodiment as well as the first embodiment, because the conductive film 76 is provided on the ultrasonic wave radiation side of the cMUT chip 20 as a ground layer, the electric safety of the ultrasonic probe 2b to the subject can improve. Moreover, in the third embodiment, a sealant need not be separately formed around the wire 86.

6. Fourth Embodiment

Figure 9:
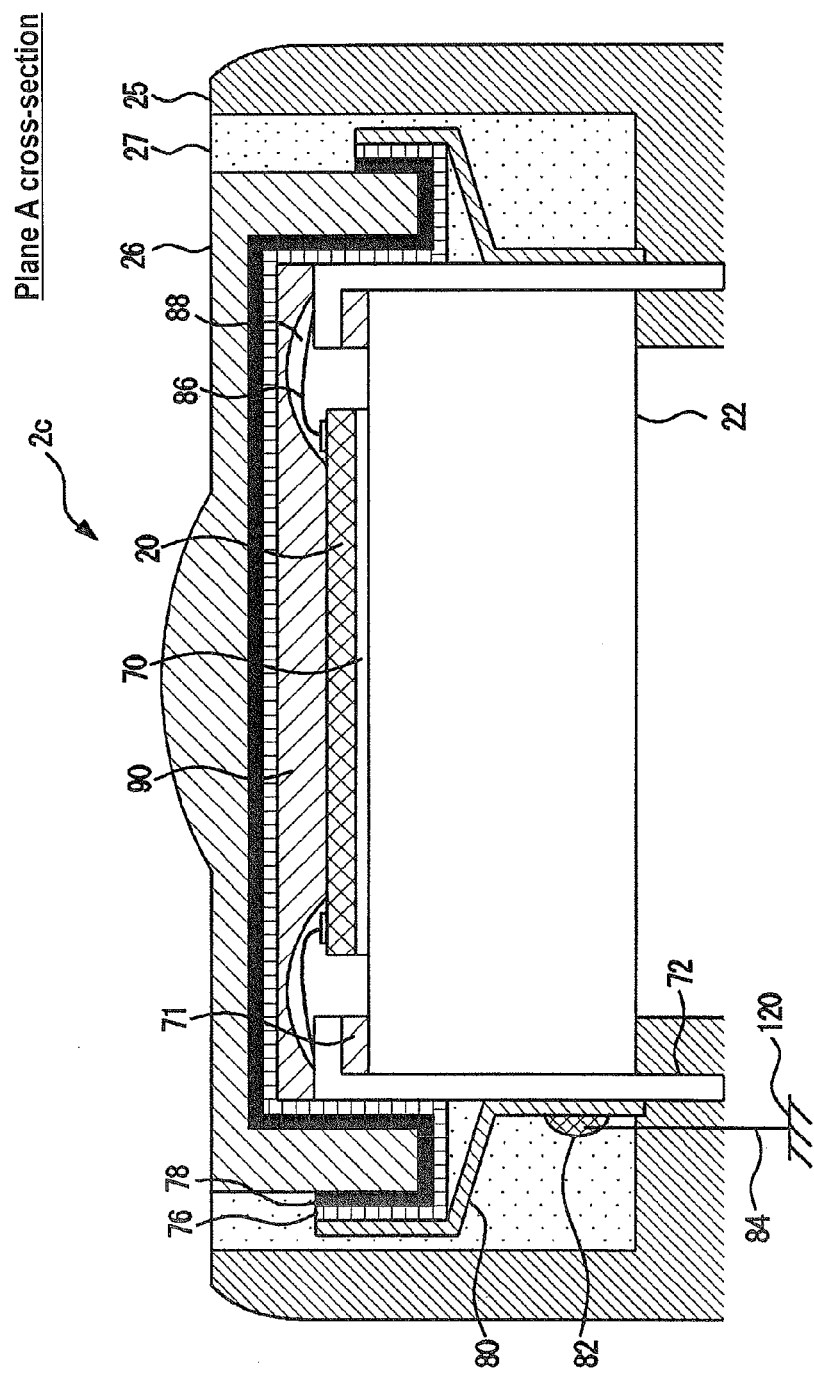
FIG. 9 is a view showing an ultrasonic probe 2c according to the fourth embodiment.

Next, the fourth embodiment will be described with reference to FIG. 9. FIG. 9 is a view showing the ultrasonic probe 2c according to the fourth embodiment. FIG. 9 corresponds to plane A cross section of FIG. 2.

In the first embodiment, it was described that the conductive film 76 is formed on the inner surface and the outer side surface of the acoustic lens 26, however, an insulator film 78 as an insulator layer is additionally formed in the fourth embodiment. The insulator film 78 is a silicon oxide film or a pala-xylylene film, for instance.

As described above, in the fourth embodiment as well as the first embodiment, because the conductive film 76 is provided on the ultrasonic wave radiation side of the cMUT chip 20 as a ground layer, the electric safety of the ultrasonic probe 2c to the subject can improve. Moreover, in the fourth embodiment, the insulator film 78 is formed between the acoustic lens 26 and the cMUT chip 20 as an insulator layer. It is doubly insulated with the acoustic lens 26 and the insulator layer 78 between the subject and the cMUT chip 20. Therefore, the safety of the ultrasonic probe 2c improves. In addition, two or more insulator layers may be provided. For instance, two insulator layers may be provided across the conductive film 76.

7. Fifth Embodiment

Figure 10:
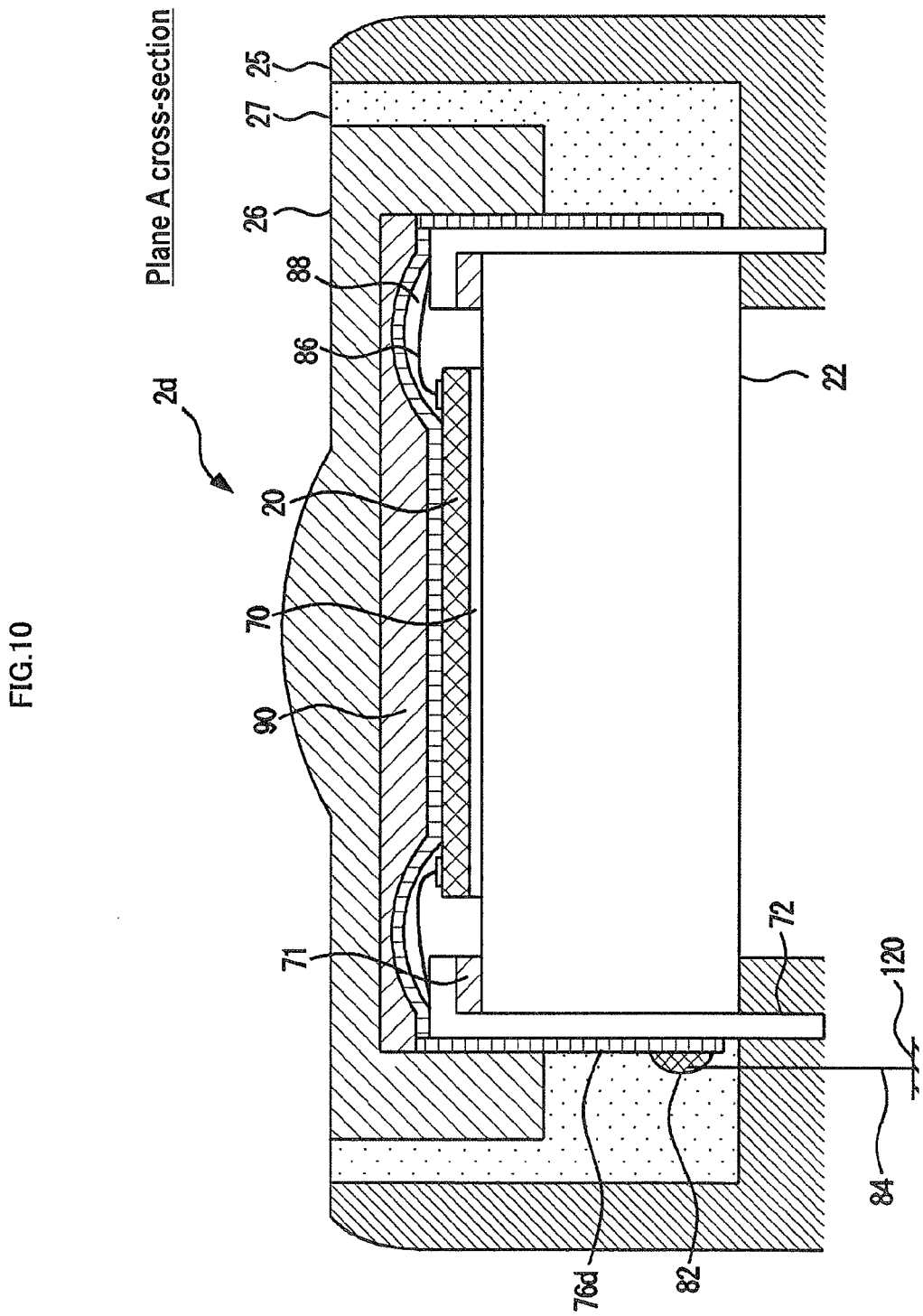
FIG. 10 is a view showing an ultrasonic probe 2d according to the fifth embodiment.

Next, the fifth embodiment will be described with reference to FIG. 10. FIG. 10 is a view showing the ultrasonic probe 2d according to the fifth embodiment. FIG. 10 corresponds to plane A cross section of FIG. 2.

In the first embodiment, it was described that the conductive film 76 is formed on the inner surface and the outer side surface of the acoustic lens 26, however the conductive film 76d is formed along the ultrasonic wave radiation surface of the cMUT chip 20 and the side surfaces of the flexible substrate 72 and the backing layer 22 in the fifth embodiment.

As described above, in the fifth embodiment as well as the first embodiment, because the conductive film 76d is provided on the ultrasonic wave radiation side of the cMUT chip 20 as a ground layer, the electric safety of the ultrasonic probe 2d to the subject can improve. Moreover, in the fifth embodiment, because the conductive film 76d is formed on the ultrasonic wave radiation surface of the cMUT chip 20, a conductive film does not need to be formed on the inner surface and the outer side surface of the acoustic lens 26. Moreover, because the conductive film 76d is formed along the side surfaces of the flexible substrate 72 and the backing layer 22, the conductive film 76d and the ground line 84 can be directly connected through the connecting portion 82 based on the backing layer 22.

8. Sixth Embodiment

Figure 11:
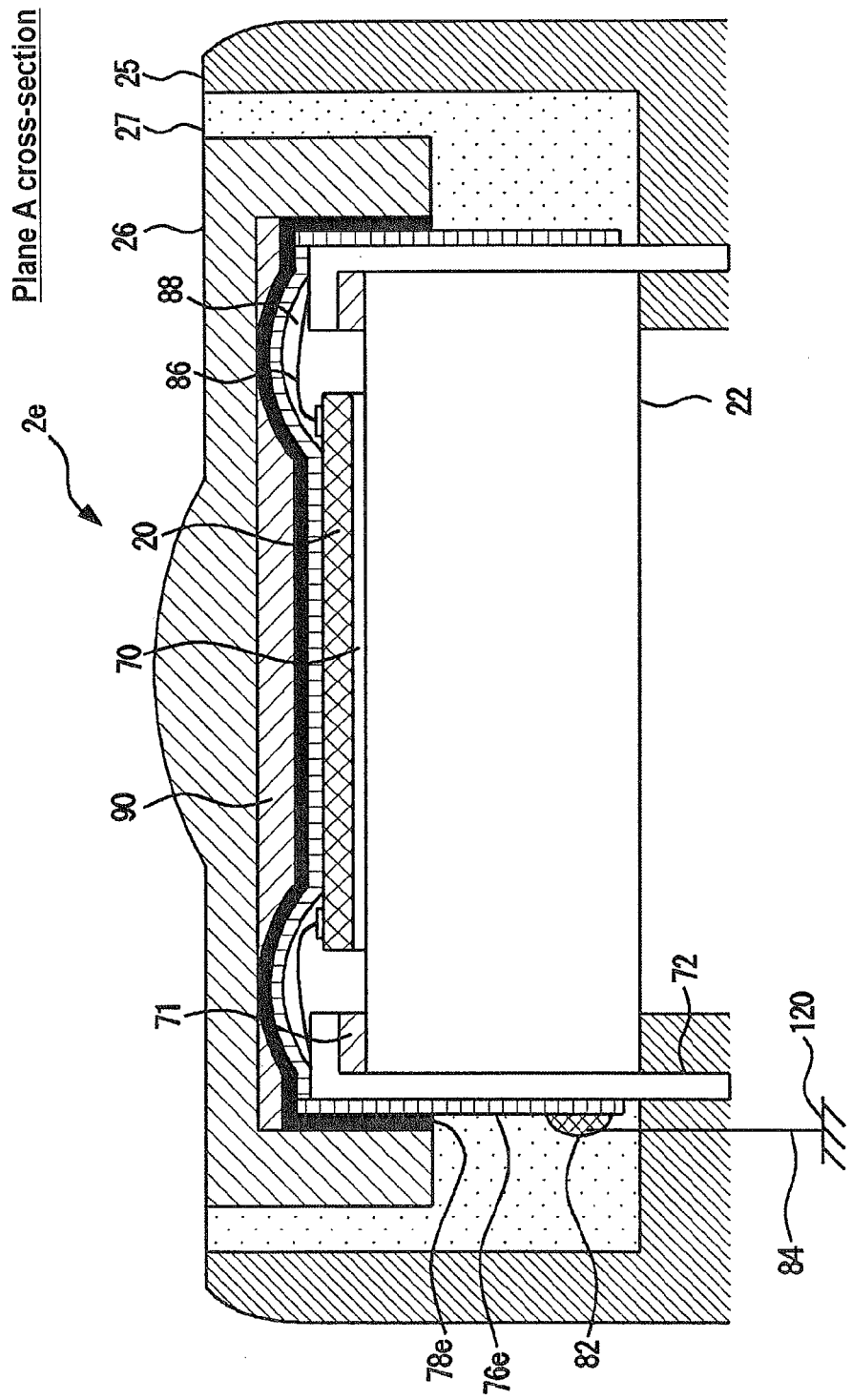
FIG. 11 is a view showing an ultrasonic probe 2e according to the sixth embodiment.

Next, the sixth embodiment will be described with reference to FIG. 11. FIG. 11 is a view showing the ultrasonic probe 2e according to the sixth embodiment. FIG. 11 corresponds to plane A cross section of FIG. 2.

In the fifth embodiment, it was described that the conductive film 76d is formed on the ultrasonic wave radiation surface of the cMUT chip 20, however, an insulator film 78e is additionally formed as an insulator layer in the sixth embodiment. That is, the conductive film 76e and the insulator film 78e are formed on the ultrasonic wave radiation surface of the cMUT chip 20.

As described above, in the sixth embodiment as well as the fifth embodiment, the insulator film 78e is formed between the acoustic lens 26 and the cMUT chip 20 as an insulator layer. It is doubly insulated with the acoustic lens 26 and the insulator layer 78e between the subject and the cMUT chip 20. Therefore, the safety of the ultrasonic probe 2e improves. In addition, two or more insulator layers may be provided. For instance, two insulator layers may be provided across the conductive film 76e.

9. Seventh Embodiment

Figure 12:
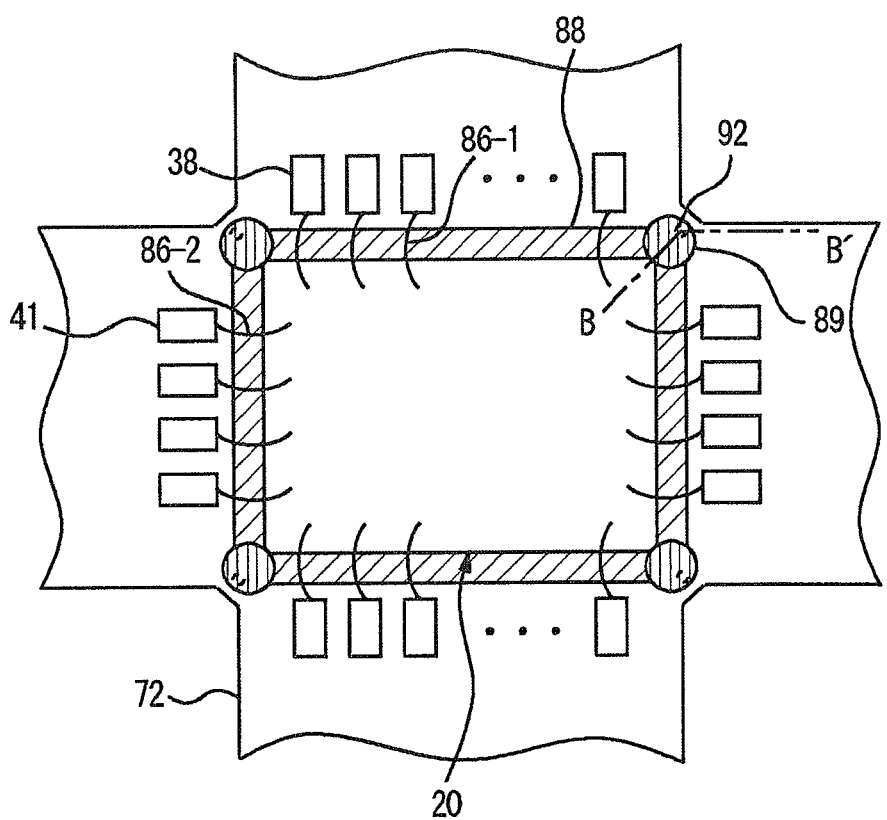
FIG. 12 is a schematic view showing the wiring of the ultrasonic probe 2.
Figure 13:
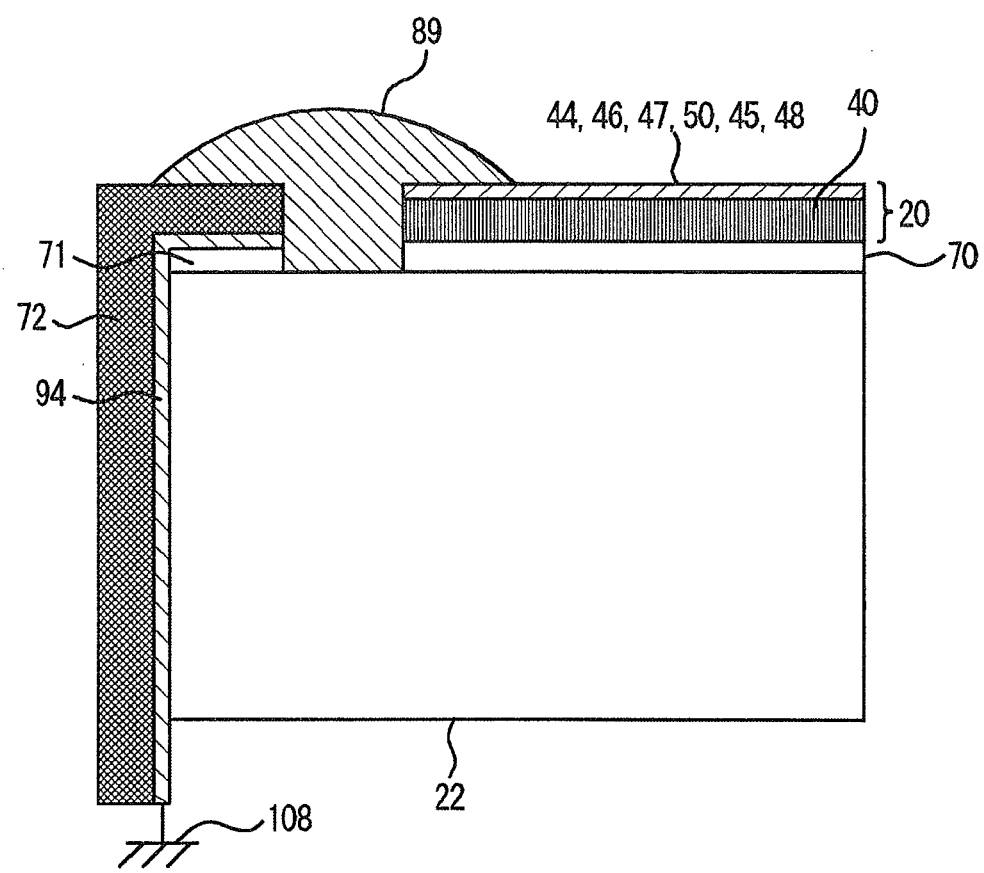
FIG. 13 is a view showing the ground connection of a substrate 40 of a cMUT chip 20.

Next, the seventh embodiment will be described with reference to FIG. 12 and FIG. 13. FIG. 12 is a schematic view showing the wiring of the ultrasonic probe 2. FIG. 13 is a view showing the ground connection of the substrate 40 of the cMUT chip 20. FIG. 13 is cross section of FIG. 12 along the B-B' line.

In an upper periphery of the cMUT chip 20, the upper electrode 46 of the cMUT chip 20 and a signal pattern 38 of the flexible substrate 72 is connected through a wire 86-1, and the lower electrode 48 of the cMUT chip 20 and a signal pattern 41 of the flexible substrate 72 are connected through a wire 86-2. Light curing resin 88 is filled around the wire 86 and a connecting portion is sealed.

In the corner portion (angle portion) of the cMUT chip 20, conductive resin 89 is filled between the cMUT chip 20 and the flexible substrate 72. The conductive resin 89 corresponds to a connecting portion of the substrate 40 of cMUT chip 20 and a ground line 94. The ground line 94 is set between the flexible substrate 72 and the backing layer 22 at the corner portion of the cMUT chip 20.

The substrate 40 is provided on the bottom of the cMUT chip 20. The substrate 40 is electrically connected with the conductive resin 89. The substrate 40 is connected with the ground 108 through the conductive resin 89 and the ground line 94. In addition, the ground line 94 in FIG. 13 corresponds to the wiring 87 of FIG. 6. The conductive resin 89 is provided at the connecting portion of the substrate 40 and the wiring 87.

As described above, in the seventh embodiment, the substrate 40 of the cMUT chip 20 is connected with ground 108 through the conductive resin 89 and the grand line 94 at the corner portion. As a result, the ultrasonic wave characteristics can be stabilized by stabilizing the potential of the cMUT chip 20 without being the upper electrode 46 at ground potential.

Moreover, there is the wire 86 which connects the cMUT chip 20 and the signal pattern 38 and the signal pattern 41 of the flexible substrate 72 in the periphery except for the corner portion of the cMUT chip 20, and the substrate 40 of the cMUT chip 20 and the ground line 94 is connected through the conductive resin 89 filled in the corner portion of the cMUT chip 20. As a result, a signal pattern connecting portion and a substrate ground connecting portion can be provided independently at different locations, and manufacturing is also easy.

In addition, because the substrate 40 itself is also semiconductor, there is a possibility that the substrate 40 becomes at a high voltage when some accident occurs. In the seventh embodiment, because the substrate 40 is connected with the ground, the substrate 40 can be maintained at the ground voltage when some accident occurs, and the safety of the ultrasonic probe 2 can be secured.

10. Eighth Embodiment

Figure 14:
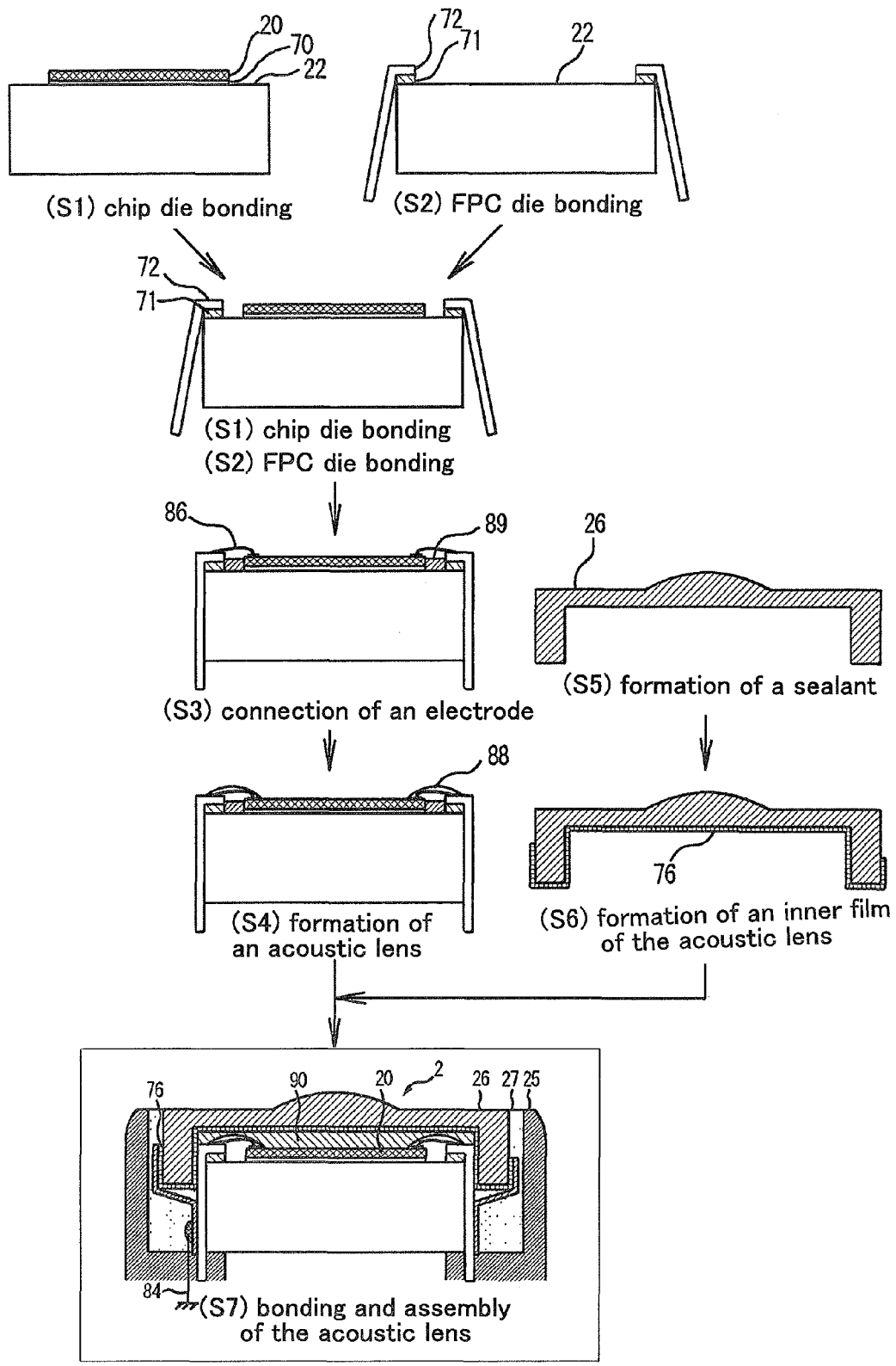
FIG. 14 is a view showing the manufacturing process of the ultrasonic probe 2 shown in FIG. 5.

Next, the eighth embodiment will be described with reference to FIG. 14. The eighth embodiment relates to a method for manufacturing the ultrasonic probe 2 of FIG. 5, the ultrasonic probe 2b of FIG. 8 and the ultrasonic probe 2c of FIG. 9. FIG. 14 is a view showing the manufacturing process of the ultrasonic probe 2 shown in FIG. 5

The cMUT chip 20 is bonded on the upper surface of the backing layer 22 with the bonding layer 70 (step S1). The flexible substrate 72 is bonded on an upper periphery of the backing layer 22 with the bonding layer 71 (step S2). The flexible substrate 72 and the cMUT chip 20 are electrically connected through the wire 86. The wire 86 is connected by using a wire bonding method or a flip chip bonding method (step S3). The light curing resin 88 is filled around the wire 86 as a sealant (step S4).

The acoustic lens 26 is formed (step S5), and the conductive film 76 is formed on an inner surface of the acoustic lens 26 (step S6). The acoustic lens 26 is bonded on the ultrasonic wave radiation surface of the cMUT chip 20 with the bonding layer 90. The conductive film 76 is connected with the ground line 84. The ultrasonic probe cover 25 is attached. The sealant 27 is filled in the space between the acoustic lens 26, the flexible substrate 72, and the ultrasonic probe cover 25 (step S7).

The ultrasonic probe 2 shown in FIG. 5 is manufactured through the above-mentioned process. In addition, the process in step S4 may be omitted and the bonding layer 90 may be filled around the wire 86 and may be concurrently used as an adhesive and a sealant. In this case, the ultrasonic probe 2b shown in FIG. 8 is manufactured. Moreover, the conductive film 76 and the insulator film 78 may be simultaneously formed in step S6. In this case, the ultrasonic probe 2c shown in FIG. 9 is manufactured.

As for a method of forming the film, there are a method for shaping the acoustic lens 26 and in mold shaping an insulator sheet with a conductive film simultaneously and a method for forming an insulator film or a conductive film by a physical deposition or a chemical deposition. By the in-mold shaping, though the film can be formed at low cost, film thickness of about 10 μm is a limit. On the other hand, film thickness of about 1 μm can be obtained in the film formation by the deposition.

11. Ninth Embodiment

Figure 15:
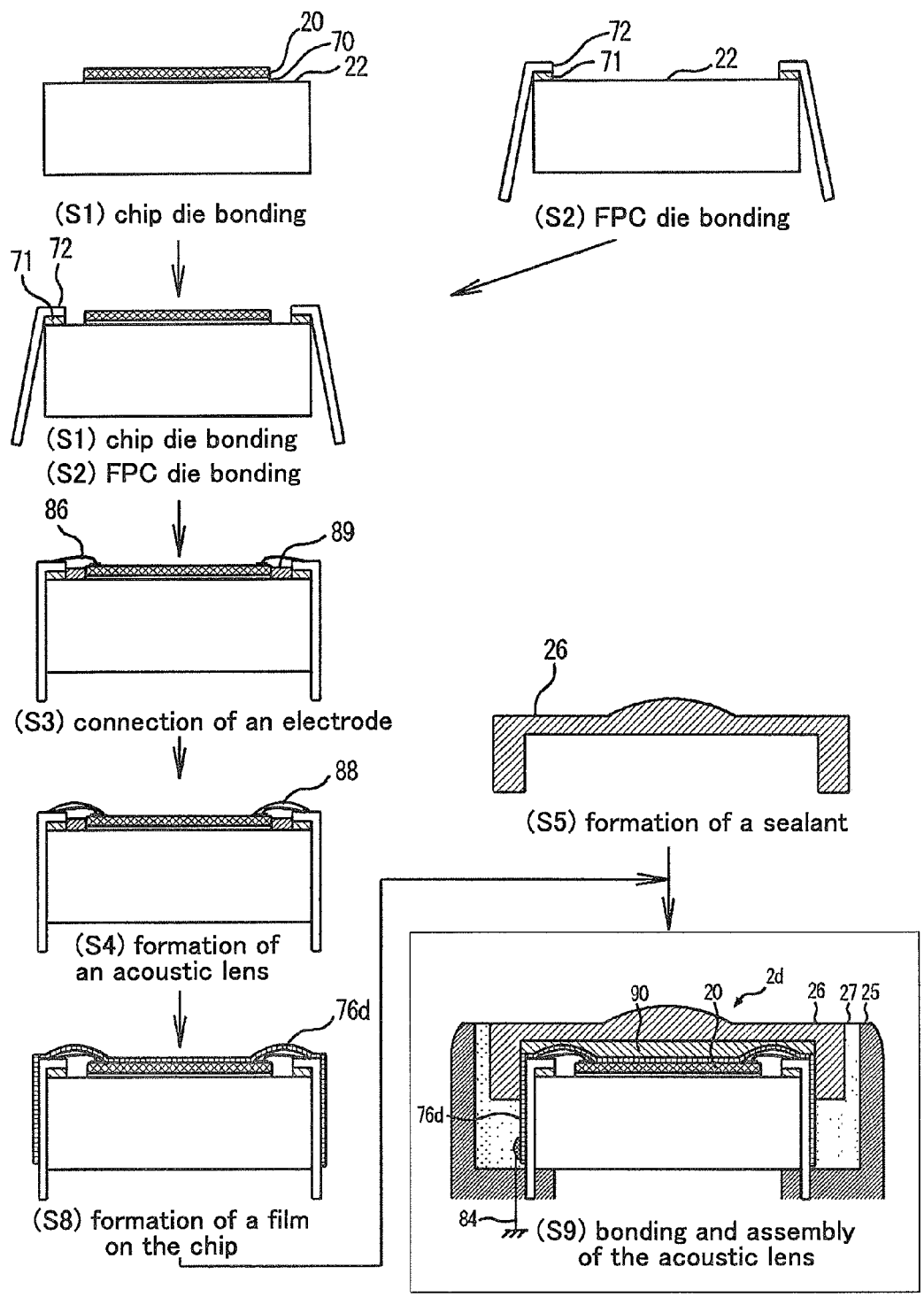
FIG. 15 is a view showing the manufacturing process of the ultrasonic probe 2d shown in FIG. 10.

Next, the ninth embodiment will be described with reference to FIG. 15. The ninth embodiment relates to the method for manufacturing the ultrasonic probe 2d of FIG. 10 and the ultrasonic probe 2e of FIG. 11. FIG. 15 is a view showing the manufacturing process of the ultrasonic probe 2d shown in FIG. 10.

It is described that a conductive film and an insulator film are formed on the side of the acoustic lens 26 in the eighth embodiment, however, a conductive film and an insulator film is formed on the side of the cMUT chip 20 in the ninth embodiment.

Because the process from the step S1 to the step S5 is similar to FIG. 14, the explanation is omitted. The conductive film 76d is formed along the ultrasonic wave radiation surface of the cMUT chip 20 and the side surfaces of the flexible substrate 72 and the backing layer 22 (step S8). The acoustic lens 26 is bonded on the ultrasonic wave radiation surface of the cMUT chip 20 with the bonding layer 90. The conductive film 76d is connected with the ground line 84. The ultrasonic probe cover 25 is provided. The sealant 27 is filled in the space between the acoustic lens 26, the flexible substrate 72 and the ultrasonic prove cover 25 (step S9).

The ultrasonic probe 2d shown in FIG. 10 is manufactured through the above-mentioned process. In addition, the conductive film 76e and the insulator film 78e may be simultaneously formed in step S8. In this case, the ultrasonic probe 2e shown in FIG. 11 is manufactured.

12. Tenth Embodiment

Figure 16:
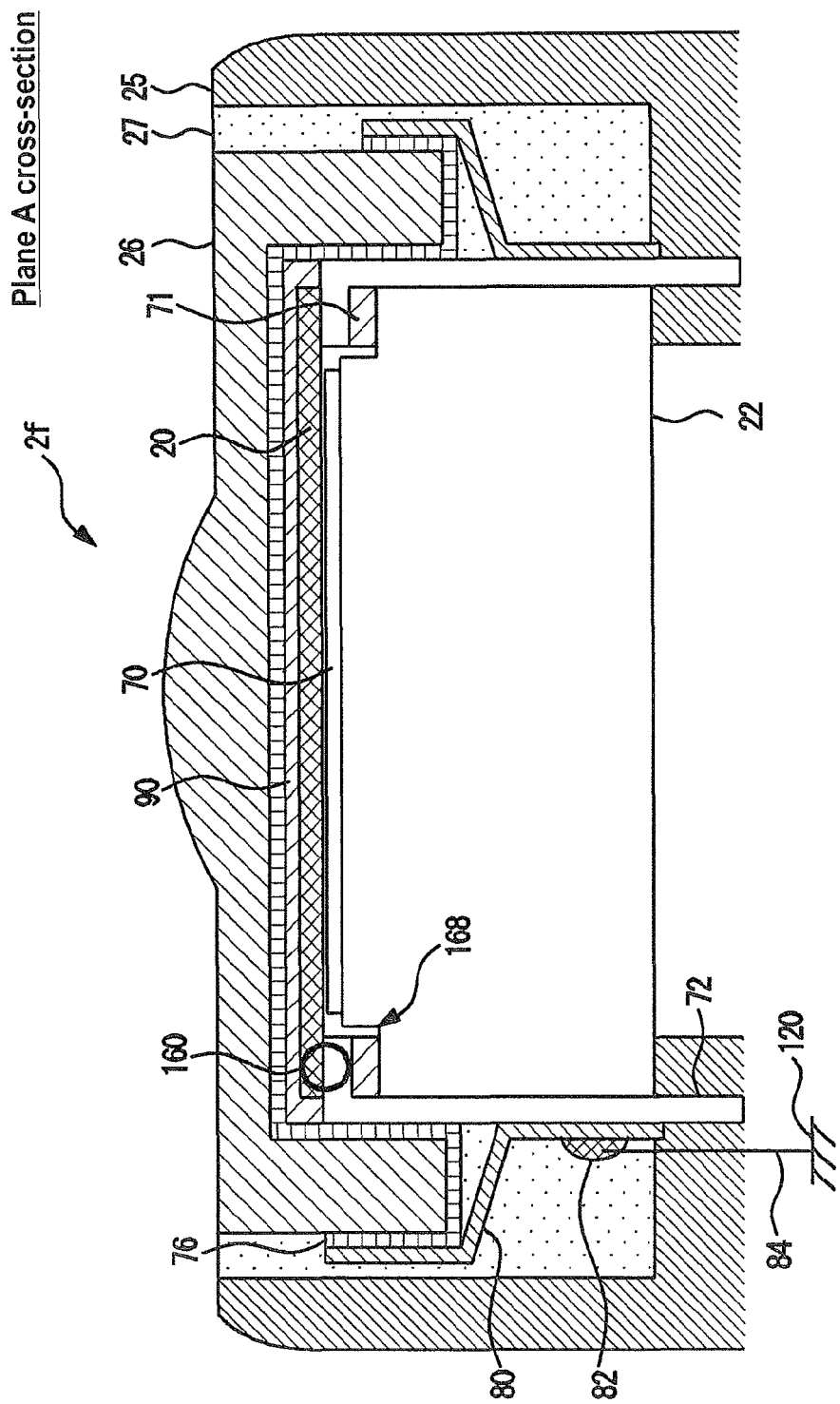
FIG. 16 is a view showing an ultrasonic probe 2f according to the tenth embodiment.
Figure 17:
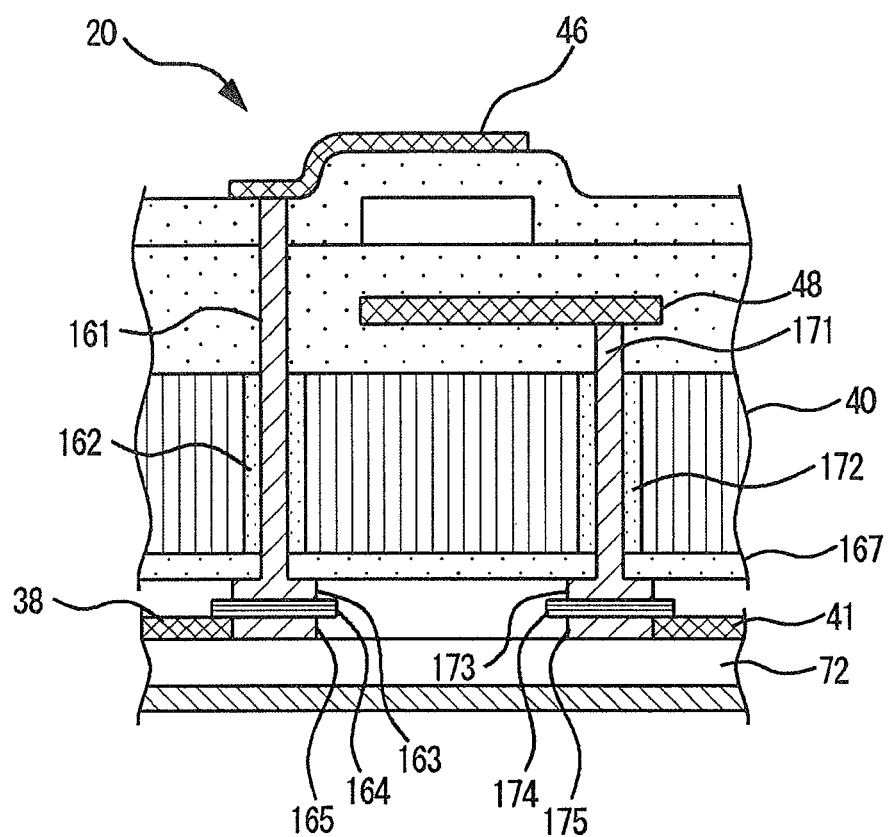
FIG. 17 is a detail view of the electrical connection part 160 shown in FIG. 16.

Next, the tenth embodiment will be described with reference to FIG. 16 and FIG. 17. The tenth embodiment relates to an electric connection of the cMUT chip 20 and the flexible substrate 72. FIG. 16 is a view showing an ultrasonic probe 2f according to the tenth embodiment. FIG. 16 corresponds to plane A cross section of FIG. 2. FIG. 17 is a detailed drawing of an electric connecting portion 160 of FIG. 16.

In the first embodiment, it is described that the flexible substrate 72 and the cMUT chip 20 are electrically connected through the wire 86 by a wire bonding method, however in the tenth embodiment, the flexible substrate 72 and the cMUT chip 20 are electrically connected through a through hole 161 or a through hole 171.

A signal pattern of the flexible substrate 72 is electrically connected with an electrode of the cMUT chip 20 on the back of the peripheral portion of the cMUT chip 20. At the electric connecting portion 160, a notch portion 168 is provided on the upper surface of peripheral portion of the backing layer 22 depending on the thickness of the flexible substrate 72, the bonding layer 71, and the bonding layer 70.

The through hole 161 is a conducting path between the upper electrode 46 of the cMUT chip 20 and a pad terminal 163 provided on the back surface of the cMUT chip 20. The through hole 171 is a conducting path between the lower electrode 48 of the cMUT chip 20 and a pad terminal 173 provided on the back surface of the cMUT chip 20. The through hole 161 and the through hole 171 are filled with metal or a metallic layer is formed on its internal wall. An insulator portion 162 and an insulator portion 172 are provided around the through hole 161 and the through hole 171 in the part of the substrate 40 of the cMUT chip 20. In addition, it is also preferable to provide an insulator layer 167 on the back surface of the substrate 40.

A pad terminal 165 and a pad terminal 175 provided on the flexible substrate 72 are respectively electrically connected with the pad terminal 163 and the pad terminal 173 provided on the lower surface of the cMUT chip 20 through a conductive adhesive 164 and a conductive adhesive 174 such as an anisotropic conductive adhesive sheet.

The signal pattern 38 of the flexible substrate 72 is electrically connected with the upper electrode 46 of the cMUT chip 20 through the pad terminal 165, the conductive adhesive 164, the pad terminal 163, and the through hole 161. The signal pattern 41 of the flexible substrate 72 is electrically connected with the lower electrode 48 of the cMUT chip 20 through the pad terminal 175, the conductive adhesive 174, the pad terminal 173, and the through hole 171.

Thus, in the tenth embodiment, the flexible substrate 72 and the cMUT chip 20 are electrically connected through the through hole 161 and the through hole 171. As a result, the flexible substrate 72 and the cMUT chip 20 can be electrically connected by only doing the alignment of pad terminals, without a wire for an electric connection.

In addition, in FIG. 17, it is described that the electric connection is achieved through a through hole on the back surface of the cMUT chip 20, however the electric connection may be achieved through a through hole on the radiation surface of the cMUT chip 20.

Moreover, when an electrode of the cMUT chip 20 and a signal line of the flexible substrate 72 are connected by the wire bonding method shown in FIG. 5 and FIG. 9 etc., because the wire 86 at high potential and the conductive film 76 at ground potential are adjacent, it is unable to maintain ground potential of the conductive film 76 with a short between the conductive film 76 and the wire 86 due to fault of a sealant such as the light curing resin 88 or pinhole fault of the insulator film 78. On the other hand, when an electrode of the cMUT chip 20 and a signal line of the flexible substrate 72 are connected by the through hole shown in FIG. 16 and FIG. 17, because a connecting line and the conductive film 76 are not adjacent, there is no fear of short, and because the ground potential of the conductive film 76 is maintained, the safety is secured.

Moreover, because the wire 86 used in the wire bonding method shown in FIG. 5 and FIG. 9 etc. is easy to be damaged by the acting force and handling is difficult because it is a thin metallic wire. On the other hand, in the connection by the through hole shown in FIG. 16 and FIG. 17, the wire connection work by the wire bonding method is unnecessary, and handling is easy.

Moreover, a sealant such as light curing resin 88 is required to fill around the wire 86, in the connection by the wire bonding method shown in FIG. 5 and FIG. 9. A resin used as a sealant and wire 86 have different coefficient of linear expansion. In general, the coefficient of linear expansion of the resin used as a sealant is larger than that of the metal. Therefore, there is fear that the wire 86 is damaged when the resin used as a sealant expands by a temperature change. Moreover, when impurities exist in the resin used as a sealant, there is fear that the spaces between the wire 86 and the conductive film 76 are short-circuited by an electric migration. On the other hand, in the connection by the through hole shown in FIG. 16 and FIG. 17, because a wire and a sealant are unnecessary, the problem originating from impurities in the resin does not occur.

As described above, in the tenth embodiment, the safety of the ultrasonic probe 2 can improve further by the connecting by the through hole in place of the connection by the wire bonding method.

13. Eleventh Embodiment

Next, the eleventh embodiment will be described with reference to FIG. 18 and FIG. 19. The eleventh embodiment relates to a ground connection of the substrate 40 of the cMUT chip 20. It is described that the substrate 40 is connected with the ground from the side surface of the cMUT chip 20 through the conductive resin 89 in the seventh embodiment, however the substrate 40 is connected with the ground from the upper side (the ultrasonic radiation side) or the lower side (the back side) of the cMUT chip 20 in the eleventh embodiment.

(13-1. Ground Connection from the Upper Side of the cMUT Chip)

Figure 18:
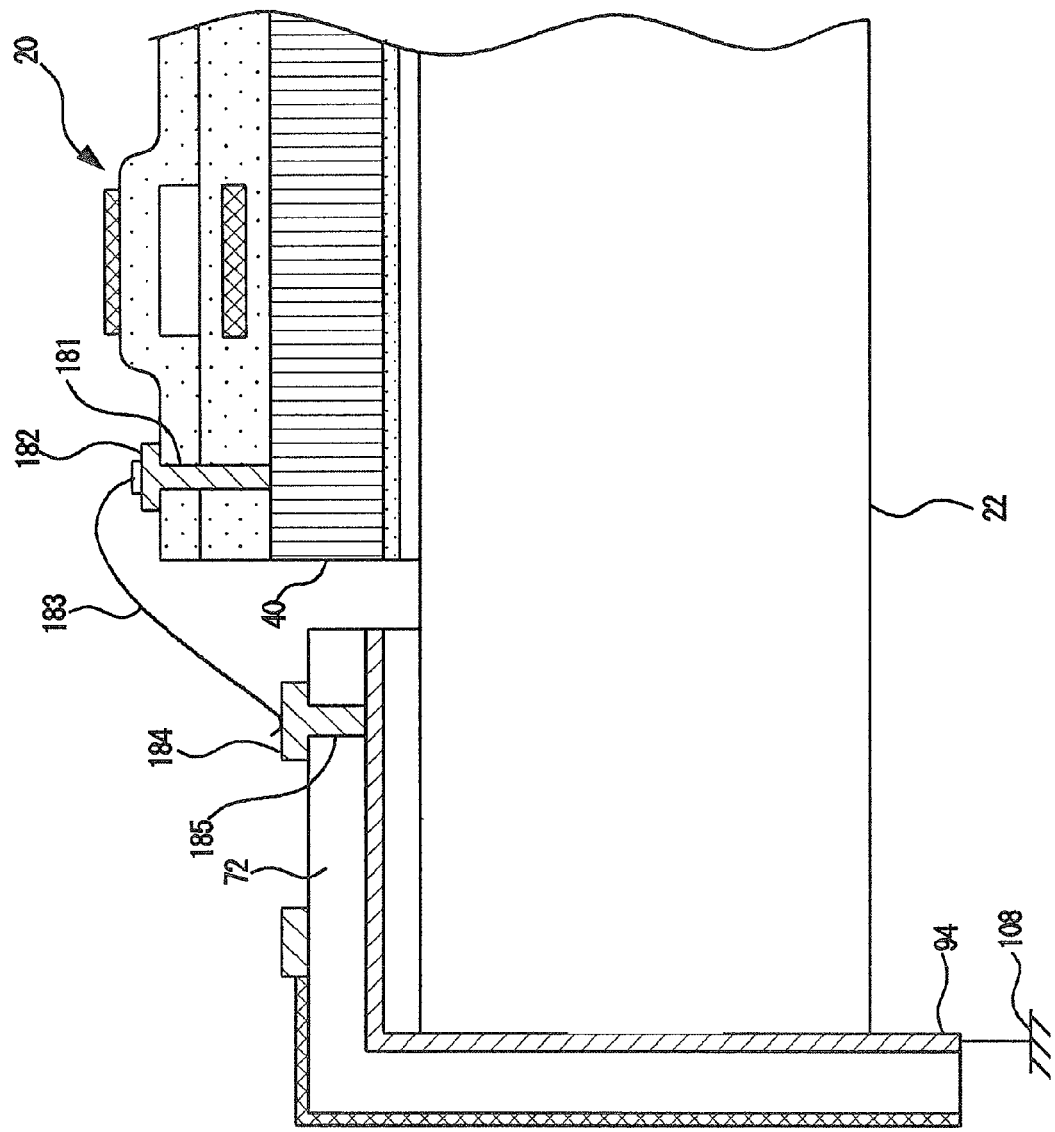
FIG. 18 is a view showing the ground connection of the substrate 40 from the upper side of the cMUT chip 20.

FIG. 18 is a view showing the ground connection of the substrate 40 from the upper side of the cMUT chip 20.

A through hole 181 is a conducting path between the substrate 40 of the cMUT chip 20 and a pad terminal 182 provided on the upper surface of the cMUT chip 20. A through hole 185 is a conducting path between the ground line 94 provided on the inner surface of the flexible substrate 72 and a pad terminal 184 provided on the upper surface. The through hole 181 and the through hole 185 are filled with metal or a metallic layer is formed on its internal wall.

The pad terminal 182 and the pad terminal 184 are electrically connected through a wire 183 by a wire bonding method. The substrate 40 of the cMUT chip 20 is connected with the ground 108 through the through hole 181, the pad terminal 182, the wire 183, the pad terminal 184, the through hole 185 and the ground line 94.

(13-2. Ground Connection from the Lower Side of the cMUT Chip)

Figure 19:
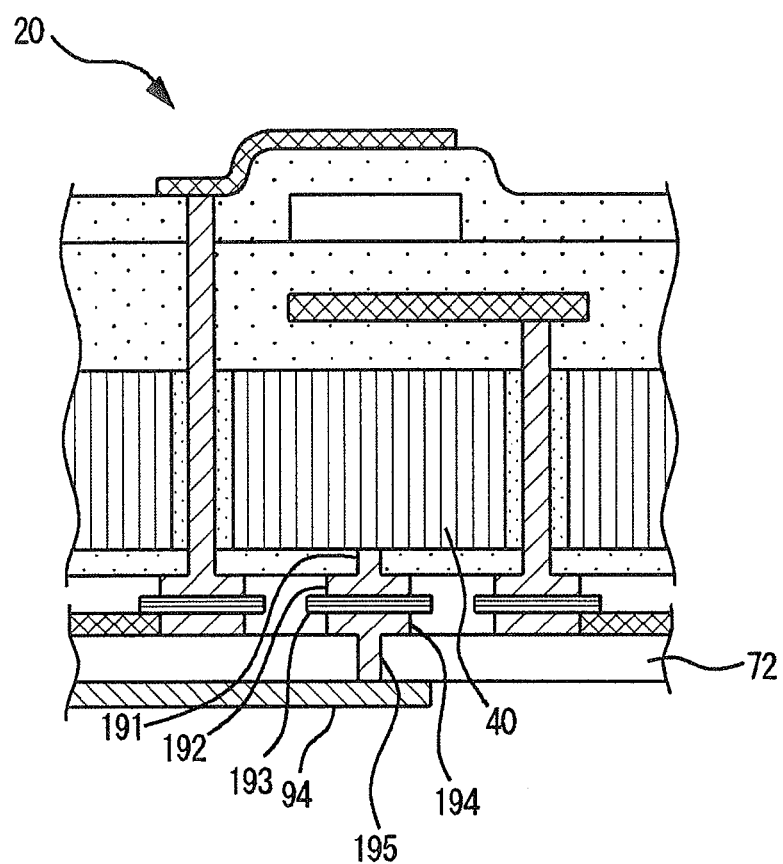
FIG. 19 is a view showing the ground connection of the substrate 40 from the lower side of the cMUT chip 20.

FIG. 19 is a view showing the ground connection of the substrate 40 from the lower side of the cMUT chip 20.

A through hole 191 is a conducting path between the substrate 40 of the cMUT chip 20 and a pad terminal 192 provided on the lower surface of the cMUT chip 20. A through hole 195 is a conducting path between the ground line 94 provided on the inner surface of the flexible substrate 72 and a pad terminal 194 provided on the upper surface. The through hole 191 and the through hole 195 are filled with metal or a metallic layer is formed on its internal wall.

A pad terminal 192 and a pad terminal 194 are electrically connected through a conductive adhesive 193 such as anisotropic conductive adhesive sheet. The substrate 40 of the cMUT chip 20 is connected with the ground through the through hole 191, the pad terminal 192, the conductive adhesive 193, the pad terminal 194, the through hole 195 and the ground line 94.

(13-3. Effect of the Eleventh Embodiment)

As described above, in the eleventh embodiment, the substrate 40 of the cMUT chip 20 can be connected with the ground from an upper side or a lower side of the cMUT chip 20 through a through hole. As a result, the substrate 40 of the cMUT chip 20 can be connected with the ground only by the connection by the wire bonding method or the alignment of pad terminals in place of the filling of the conductive resin for a ground connection. The ultrasonic wave characteristic can be stabilized by stabilizing the potential of the cMUT chip with being the substrate 40 at ground potential.

In addition, the upper electrode 46 and the lower electrode 48 applied a high voltage over 100 V exist on the substrate 40 of the cMUT chip 20. Because the substrate 40 itself is also semiconductor, there is a possibility that the substrate 40 becomes at a high voltage, when some accident occurs. In the eleventh embodiment, because the substrate 40 is connected with the ground through a through hole, even when some accident occurs, the substrate 40 can be maintained to the ground potential, so as to secure the safety of the ultrasonic probe 2.

14. Others

In addition, the ultrasonic probe and the ultrasonic diagnostic device may be composed by combining the above-mentioned embodiments properly. Moreover, in the above described embodiment, it is preferable to adjust the film thickness of a conductive layer to about 0.1 μm, and to adjust the film thickness of an insulator layer to about 1 μm. By thinning the film thickness of the insulator layer and the conductive layer respectively, the influence (influence and attenuation to the pulse and the frequency characteristics) on the ultrasonic wave transmitted/received in the cMUT chip can be controlled.

Preferred embodiments of the ultrasonic probe and the ultrasonic diagnostic device according to the present invention have been described with reference to the accompanying drawings. However, the present invention is not limited to the above-described embodiments. It is clear that a person with ordinary skill in the art can easily conceive various modifications and changes within the technical idea disclosed herein, and it is contemplated that such modifications and changes naturally fall within the technical scope of the present invention.

What is claimed is:

1. An ultrasonic probe comprising:
   a Capacitive Micromachined Ultrasonic Transducer (cMUT) chip having a plurality of vibration elements whose electromechanical coupling coefficient or a sensitivity changes depending on a bias voltage, and configured to transmit/receive an ultrasonic wave;
   an acoustic lens provided on an ultrasonic wave radiation side of said cMUT chip;
   a backing layer provided on a back side of said cMUT chip, to absorb a propagation of said ultrasonic wave;
   an electric wiring portion provided from a peripheral portion of said cMUT chip and on a side surface of said backing layer and having a signal pattern connected with an electrode of said cMUT chip arranged thereon; and
   a housing for containing said cMUT chip, acoustic lens, said backing layer and said electric wiring portion,
   wherein: a ground layer at ground potential is bonded on the ultrasonic wave radiation side of said cMUT chip;
   said cMUT chip has a substrate;
   each of said vibration elements of said cMUT chip has a film body provided on the ultrasonic radiation side of said substrate of said cMUT chip, a lower electrode provided in said film body, and an upper electrode provided on the ultrasonic radiation side of said lower electrode;
   said substrate of cMUT chip is connected with a ground;
   AC high frequency voltage transmitting/receiving ultrasonic wave is applied on said upper electrode using ground potential as reference potential; and
   DC bias voltage for changing electromechanical coupling coefficient or sensitivity of said vibration element is applied on said lower electrode using ground potential as reference potential.

2. An ultrasonic probe according to claim 1,
   wherein said ground layer is formed along the inner surface and an outer side surface of said acoustic lens;
   said ground layer and a conductive member are connected and fixed on an outer side surface of said acoustic lens; and
   said conductive member and a ground line are connected and are fixed on an side surface of said backing layer.

3. An ultrasonic probe according to claim 1,
   wherein said ground layer is formed along an inner surface and an outer side surface of said acoustic lens;
   said ground layer is fixed and connected with a ground line on an outer side surface of said acoustic lens.

4. An ultrasonic probe according to claim 1,
   wherein an insulator layer is formed on at least either an ultrasonic wave radiation side or a back side, of said ground layer.

5. An ultrasonic probe according to claim 1,
   wherein a sealant is filled around a connecting portion between an electrode of said cMUT chip and a signal pattern of said electric wiring portion.

6. An ultrasonic probe according to claim 1,
   wherein an adhesive used to bond said cMUT chip and said acoustic lens is filled around a connecting portion between an electrode of said cMUT chip and a signal pattern of said electric wiring portion.

7. An ultrasonic probe according to claim 1,
   wherein a substrate of said cMUT chip is connected with a ground line from a side of said cMUT chip through conductive resin.

8. An ultrasonic probe according to claim 1,
   wherein said cMUT chip has a through hole electrically connecting an electrode of said cMUT chip to an ultrasonic wave radiation surface or a back surface; and
   an electrode of said cMUT chip is connected with a signal pattern of said electric wiring portion through said through hole.

9. An ultrasonic probe according to claim 8,
   wherein said through hole and a signal pattern of said electric wiring portion are connected by an alignment of both pad terminals.

10. An ultrasonic probe according to claim 1,
    wherein said cMUT chip has a through hole electrically connecting a substrate of said cMUT chip to an ultrasonic wave radiation surface or a back surface; and
    a substrate of said cMUT chip is connected with a ground line through said through hole.

11. An ultrasonic diagnostic device comprising:
    an ultrasonic probe transmitting/receiving an ultrasonic wave to a subject;
    an image processing part producing an ultrasonic wave image based on a received ultrasonic wave signal output from said ultrasonic probe; and
    a display part displaying said ultrasonic wave image,
    wherein said ultrasonic probe is a probe according to claim 1.

12. An ultrasonic probe comprising:
    a Capacitive Micromachined Ultrasonic Transducer (cMUT) chip having a plurality of vibration elements whose electromechanical coupling coefficient or a sensitivity changes depending on a bias voltage, and configured to transmit/receive an ultrasonic wave to/from a subject;
    an acoustic lens provided on an ultrasonic wave radiation side of said cMUT chip;
    a backing layer provided on a back side of said cMUT chip, to absorb a propagation of said ultrasonic wave;
    an electric wiring portion provided from a peripheral portion of said cMUT chip and on a side surface of said backing layer and having a signal pattern connected with an electrode of said cMUT chip arranged thereon; and
    a housing for containing said cMUT chip, acoustic lens, said backing layer and said electric wiring portion,
    wherein: a ground layer at ground potential surrounds the ultrasonic wave radiation side of said cMUT chip and side surfaces of said cMUT chip and said electrical wiring portion, to cover said cMUT chip and said side surfaces of said electrical wiring portion as a grounding barrier to not allow electricity in the ultrasonic probe to discharge to the subject;

said cMUT chip has a substrate;

each of said vibration elements of said cMUT chip has a film body provided on the ultrasonic radiation side of said substrate of said cMUT chip, a lower electrode provided in said film body, and an upper electrode provided on the ultrasonic radiation side of said lower electrode;

said substrate of cMUT chip is connected with a ground line;

AC high frequency voltage for transmitting/receiving ultrasonic wave is applied on said upper electrode using ground potential as reference potential; and DC bias voltage for changing electromechanical coupling coefficient or sensitivity of said vibration element is applied on said lower electrode using ground potential as reference potential.

13. An ultrasonic probe according to claim 12,
wherein said ground layer is formed along the inner surface and an outer side surface of said acoustic lens;
said ground layer and a conductive member are connected and fixed on an outer side surface of said acoustic lens; and
said conductive member and a ground line are connected and are fixed on an side surface of said backing layer.

14. An ultrasonic probe according to claim 12,
wherein said ground layer is formed along an inner surface and an outer side surface of said acoustic lens;
said ground layer is fixed and connected with a ground line on an outer side surface of said acoustic lens.

15. An ultrasonic probe according to claim 12,
wherein an insulator layer is formed on at least either an ultrasonic wave radiation side or a back side, of said ground layer.

16. An ultrasonic probe according to claim 12,
wherein a sealant is filled around a connecting portion between an electrode of said cMUT chip and a signal pattern of said electric wiring portion.

17. An ultrasonic probe according to claim 12,
wherein an adhesive used to bond said cMUT chip and said acoustic lens is filled around a connecting portion between an electrode of said cMUT chip and a signal pattern of said electric wiring portion.

18. An ultrasonic probe according to claim 12,
wherein a substrate of said cMUT chip is connected with a ground line from a side of said cMUT chip through conductive resin.

19. An ultrasonic probe according to claim 12,
wherein said cMUT chip has a through hole electrically connecting an electrode of said cMUT chip to an ultrasonic wave radiation surface or a back surface; and
an electrode of said cMUT chip is connected with a signal pattern of said electric wiring portion through said through hole.

20. An ultrasonic probe according to claim 19,
wherein said through hole and a signal pattern of said electric wiring portion are connected by an alignment of both pad terminals.

21. An ultrasonic probe according to claim 12,
wherein said cMUT chip has a through hole electrically connecting a substrate of said cMUT chip to an ultrasonic wave radiation surface or a back surface; and
a substrate of said cMUT chip is connected with a ground line through said through hole.

* * * * *